US006760609B2

(12) United States Patent
Jacques

(10) Patent No.: US 6,760,609 B2
(45) Date of Patent: *Jul. 6, 2004

(54) ADAPTIVE CALIBRATION PULSED OXIMETRY METHOD AND DEVICE

(75) Inventor: Steven L. Jacques, Portland, OR (US)

(73) Assignee: Providence Health System - Oregon, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/196,715

(22) Filed: Jul. 15, 2002

(65) Prior Publication Data

US 2003/0109776 A1 Jun. 12, 2003

Related U.S. Application Data

(63) Continuation-in-part of application No. 09/616,465, filed on Jul. 14, 2000, now Pat. No. 6,421,549.
(60) Provisional application No. 60/143,894, filed on Jul. 14, 1999.

(51) Int. Cl.[7] ................................................. A61B 5/00
(52) U.S. Cl. ...................... 600/331; 600/323; 600/330
(58) Field of Search ............................... 600/322–323, 600/331, 309–310

(56) References Cited

U.S. PATENT DOCUMENTS

| | | |
|---|---|---|
| RE28,990 E | 10/1976 | Hon et al. |
| 4,086,915 A | 5/1978 | Kofsky et al. |
| 4,407,290 A | 10/1983 | Wilber |
| 4,807,631 A | 2/1989 | Hersh et al. |
| 4,819,646 A | 4/1989 | Cheung et al. |
| 4,892,101 A | 1/1990 | Cheung et al. |
| 5,111,817 A | 5/1992 | Clark et al. |
| 5,411,024 A | 5/1995 | Thomas et al. |
| 5,431,159 A | 7/1995 | Baker et al. |
| 5,448,991 A | 9/1995 | Polson et al. |
| 5,725,480 A | 3/1998 | Oosta et al. ................. 600/310 |
| 5,772,589 A * | 6/1998 | Bernreuter ................... 600/323 |
| 5,820,550 A | 10/1998 | Polson et al. |
| 5,922,607 A * | 7/1999 | Bernreuter ................... 436/68 |
| 6,064,898 A | 5/2000 | Aldrich |
| 6,151,107 A | 11/2000 | Schollermann et al. ........ 356/41 |
| 6,226,540 B1 | 5/2001 | Bernreuter ................... 600/323 |
| 6,421,549 B1 * | 7/2002 | Jacques ....................... 600/331 |
| 6,493,565 B1 * | 12/2002 | Chance et al. .............. 600/310 |

* cited by examiner

Primary Examiner—Mary Beth Jones
Assistant Examiner—Matthew Kremer
(74) Attorney, Agent, or Firm—Marger Johnson & McCollom, PC

(57) ABSTRACT

A method for determining an arterial blood oxygen saturation level according to this invention includes measuring the light transmittance through tissue of light of a first wavelength and a second wavelength. A steady-state component of the measured light transmission is used to select an appropriate calibration curve. A pulsatile component of the measured light transmission is used to determine the arterial blood oxygen saturation level using the selected calibration curve. An oximetry system is also provided. An improved oximetry system is further provided wherein a plurality of light transmission measurements are used to determine a blood oxygen saturation level.

12 Claims, 16 Drawing Sheets

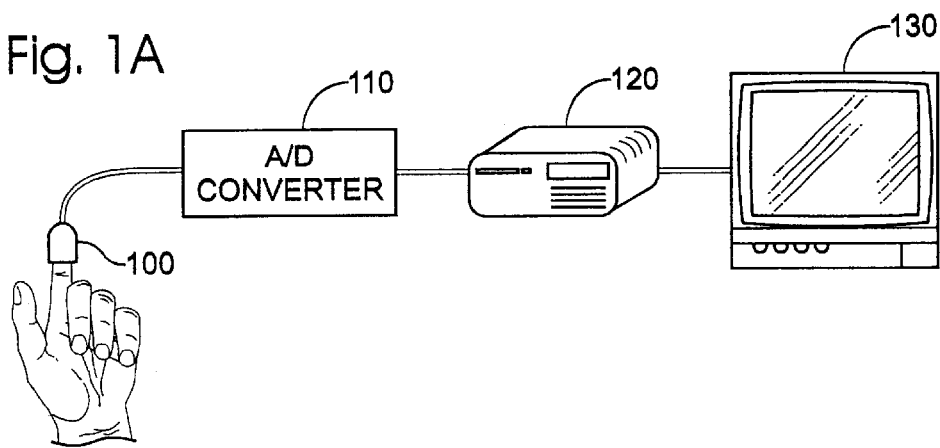
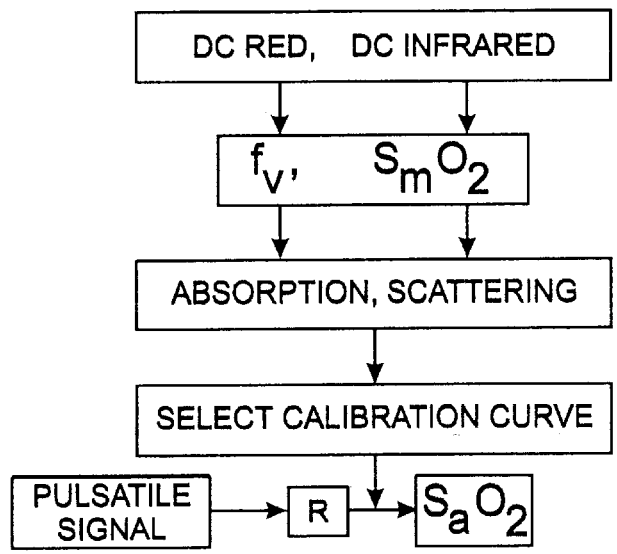

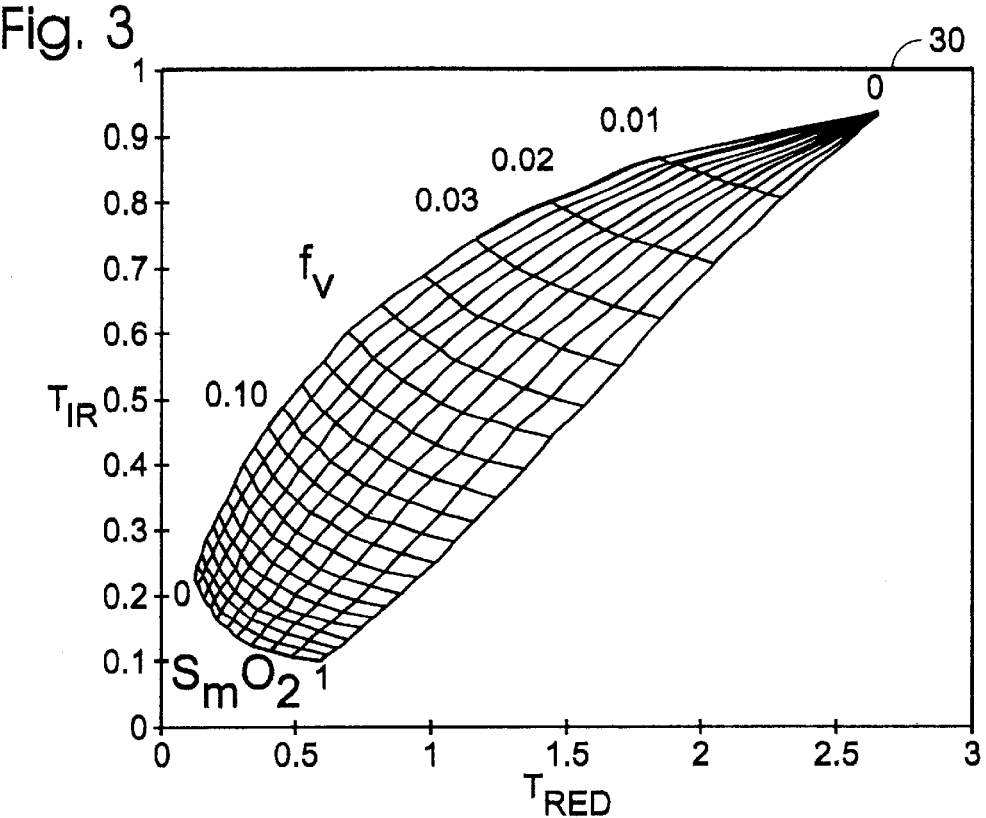
Fig. 3
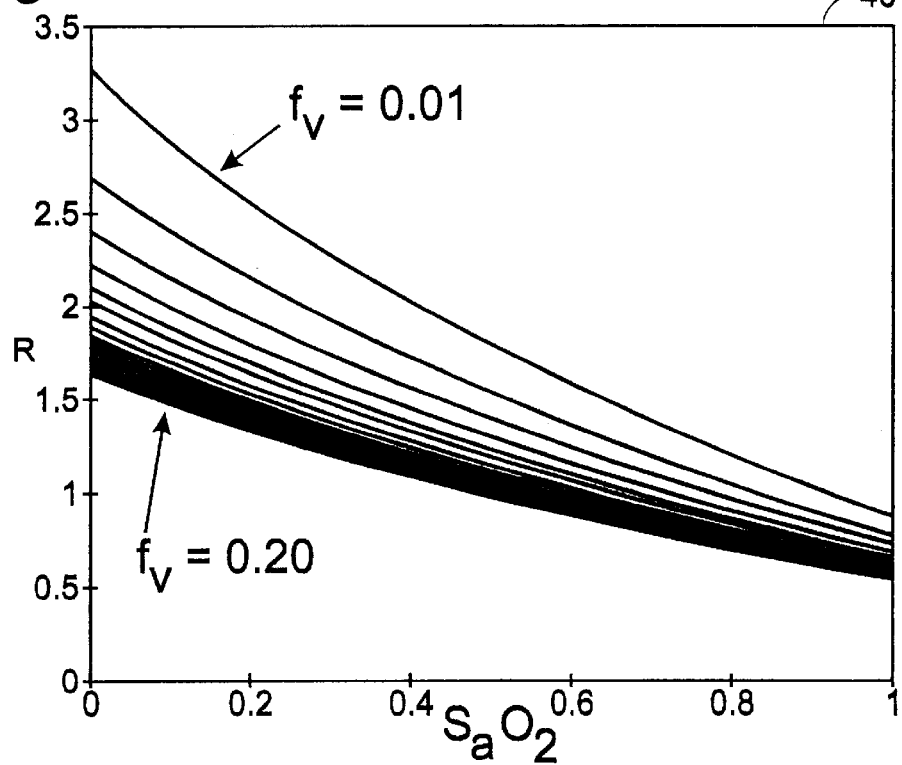
Fig. 4 CALIBRATION CURVES

```
% calibrate.m clear

%%%%%%%
% Load nm(), oxyblood(), deoxyblood(), bloodless(),
% musp_dermis(), musp_blood() for 250:2:1000 nm = (1:376).
% Retain only the optical properties at 730 and 940 nm.
%%%%
tissueoptics
i730 = 241;            % index: nm(i_730) = 730
i940 = 346;            % index: nm(i_940) = 940
oxy(1:2) = [oxyblood(i730) oxyblood(i940)];
deoxy(1:2) = [deoxyblood(i730) deoxyblood(i940)];
skin(1:2) = [bloodless(i730) bloodless(i940)];
musp_skin(1:2) = [musp_dermis(i730) musp_dermis(i940)];
musp_bl(1:2) = [musp_blood(i730) musp_blood(i940)];
clear nm oxyblood deoxyblood bloodless musp_dermis musp_blood;
```

© Providence Health System - Oregon

FIG. 5A

```
figure for i = 1:20
        fv = i*0.01;   % choose series of blood volume fractions for j = 1:51
                SaO2 = (j-1)/50;   % choose series of SaO2 values
                SmO2 = SaO2*0.80;  % choose SmO2 = fraction of SaO2
                        % Note: SmO2 <= SaO2.

mua_arterial =  SaO2*oxy + (1-SaO2)*deoxy;
                mua_mixed    = fv*( SmO2*oxy + (1-SmO2)*deoxy ) + (1-fv)*skin;

musp = fv*musp_bl + (1-fv)*musp_skin;
                optprops = [musp mua_mixed mua_arterial];
                R(j) = calcR(optprops);
                SO2(j) = SaO2;

end % j
        plot(SO2, R,'y')
        hold on
        if (i==1);plot(SO2, R,'r-');end end % i xlabel('SaO2')
ylabel('R')
title('CALIBRATION CURVES')
axis([0 1 0 3.5])

© Providence Health System - Oregon
```

FIG. 5B

% calcR.m function R = calcR(optprops)

musp = optprops(1:2);
mua_mixed = optprops(3:4);
mua_arterial = optprops(5:6);

d = 0.55;

for j=1:2  % 1=red, 2=infrared mua = mua_mixed(j);
D = 1/(mua + musp(j))/3;
delta = sqrt(D/mua);
T1(j) = exp(-d/delta)/(4*pi*D*d);

mua = mua_mixed(j) + 0.001*mua_arterial(j);
D = 1/(mua + musp(j))/3;
delta = sqrt(D/mua);
T2(j) = exp(-d/delta)/(4*pi*D*d);

end %j

%%%%%%
% Calculate R
%%%
A_730 = (T2(1) - T1(1))*2/(T2(1) + T1(1));  % RED
A_940 = (T2(2) - T1(2))*2/(T2(2) + T1(2));  % INFRARED
R = A_730/A_940;

© Providence Health System - Oregon

FIG. 6

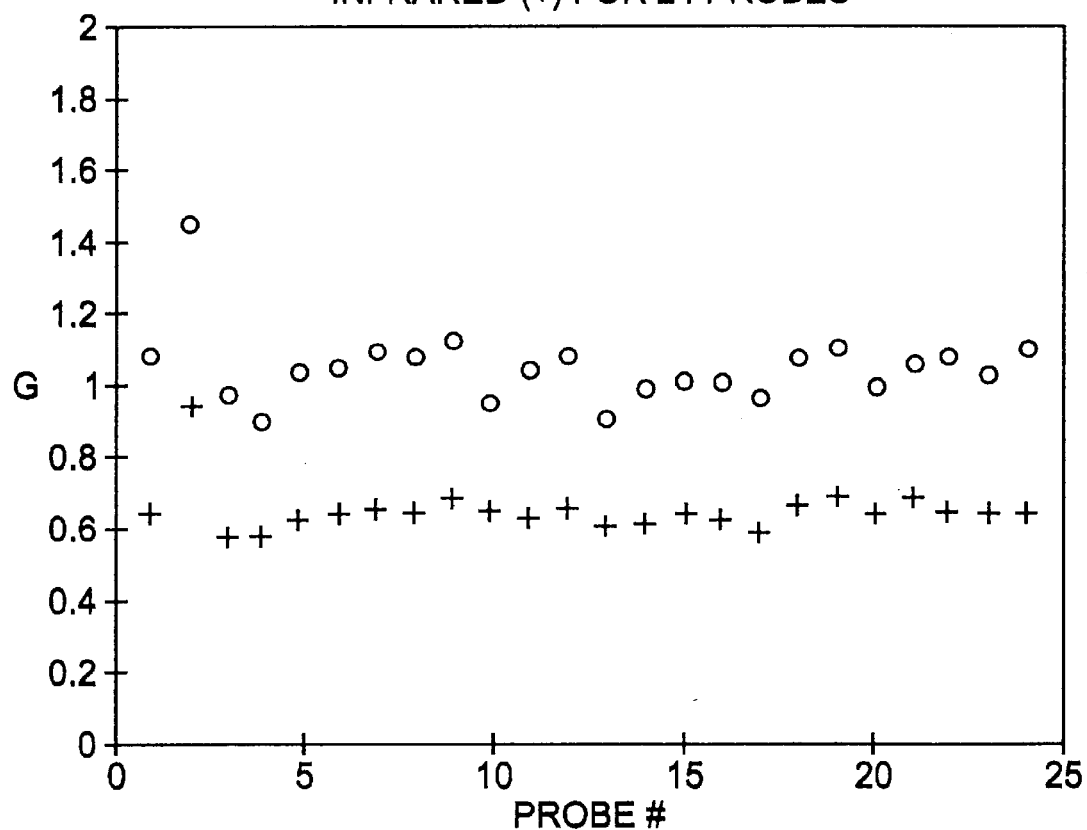

```
% calcG.m clear
close all

%%%%%%%
% Load data from IL,air experiment
%   -->  m(1:10, 1:4) = m(probe#, [REDil REDair IRil IRair])
%%%%
aircalib
m(11:24,1:4) = extra(:,1:4);

d = 0.55; % cm, effective source-detector separation
figure for i=1:24
        % red (730 nm)
        mua = 0.02;
        musp = 1.24*2;
        D = 1/3/(mua + musp);
        delta = sqrt(D/mua);
        T = exp(-d/delta)./(4*pi*D*d);
        Mil = m(i,1);
        Mair = m(i,2);
        G(i,1) = T/(Mil/Mair);
        plot(i,G(i,1),'ro')
        hold on % ir (940 nm)
        mua = 0.08;
        musp = 0.93*2;
        D = 1/3/(mua + musp);
        delta = sqrt(D/mua);
        T = exp(-d/delta)./(4*pi*D*d);
        Mil = m(i,3);
        Mair = m(i,4);
        G(i,2) = T/(Mil/Mair);
        plot(i,G(i,2),'b+')
end © Providence Health System - Oregon
```

FIG. 8A

```
xlabel('probe #')
ylabel('G')
title('G factors for red (o) and infrared (+) for 24 probes')
axis([0 25 0 2])

%%%%%
% Calculate means and standard deviations
% ignoring probe #2
%%%
['   mean   std dev']
Gred = [G(1,1) G(3:24,1)'];
red = [mean(Gred) std(Gred)]

Gir = [G(1,2) G(3:24,2)'];
ir = [mean(Gir) std(Gir)]
```

© Providence Health System - Oregon

FIG. 8B

```
% grid.m clear

%%%%%%%
% Load nm(), oxyblood(), deoxyblood(), bloodless(),
%     musp_dermis(), musp_blood() for 250:2:1000 nm = (1:376).
% Retain only the optical properties at 730 and 940 nm.
%%%%
tissueoptics
i730 = 241;                % index: nm(i_730) = 730
i940 = 346;                % index: nm(i_940) = 940
oxy(1:2) = [oxyblood(i730) oxyblood(i940)];
deoxy(1:2) = [deoxyblood(i730) deoxyblood(i940)];
skin(1:2) = [bloodless(i730) bloodless(i940)];
musp_skin(1:2) = [musp_dermis(i730) musp_dermis(i940)];
musp_bl(1:2) = [musp_blood(i730) musp_blood(i940)];
clear nm oxyblood deoxyblood bloodless musp_dermis musp_blood;

figure for i = 1:21
        fv = (i-1)*0.01;  % choose series of blood volume fractions
        fvbl(i) = fv;
        for j = 1:11
                SmO2 = (j-1)/10;   % choose series of SmO2 values
                SO2(j) = SmO2;
                mua_mixed   = fv*( SmO2*oxy + (1-SmO2)*deoxy ) + (1-fv)*skin;
                musp = fv*musp_bl + (1-fv)*musp_skin;
                optprops = [musp mua_mixed];
                result = calcDC(optprops);
                Tred(i,j) = result(1);
                Tir(i,j) = result(2);
        end % j
```

© Providence Health System - Oregon

FIG. 9A

```
end % i
plot(Tred, Tir, 'c-')
hold on for i = 1:21
        plot(Tred(i,:),Tir(i,:),'c-')
end xlabel('Tred')
ylabel('Tinfrared')
title('T_red and T_ir grid vs SmO2 and fv')
axis([0 3 0 1])

% calcDC.m function DC = calcDC(optprops)

musp = optprops(1:2);
mua_mixed = optprops(3:4);

d = 0.55;

for j=1:2  % 1=red, 2=infrared mua = mua_mixed(j);
D = 1/(mua + musp(j))/3;
delta = sqrt(D/mua);
T(j) = exp(-d/delta)/(4*pi*D*d);

end %j
```

© Providence Health System - Oregon

FIG. 9B

ADAPTIVE CALIBRATION PULSED OXIMETRY METHOD AND DEVICE

RELATED APPLICATION DATA

This application is a continuation-in-part of U.S. Ser. No. 09/616,465, filed Jul. 14, 2000, now U.S. Pat. No. 6,421,549, which claimed priority from U.S. Provisional Patent Application Serial No. 60/143,894, filed Jul. 14, 1999, both of which are incorporated herein by reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

This invention relates generally to oximeters that measure arterial blood oxygen saturation ($S_aO_2$) levels in tissues. More specifically, this invention relates to oximeters that use the pulsatile component of light of multiple wavelengths to determine the amount of arterial blood oxygen saturation.

The arterial blood oxygen saturation and pulse rate of an individual are of interest for a variety of reasons. For example, emergency or surgical care settings can use information regarding oxygen saturation to signal changing physiological factors, the malfunction of anesthesia equipment, or physician error. Similarly, in the intensive care unit, oxygen saturation information can be used to confirm the provision of proper patient ventilation or to optimize a gradual reduction and eventual removal from assisted ventilation.

The proper utilization of many lifesaving medical techniques and treatments depends upon the attending physician continually obtaining accurate and up-to-date information regarding various bodily functions of the patient. Heart rate, blood pressure, and arterial oxygen saturation are among the most critical information that a physician needs to determine an optimal course of treatment. Continuous provision of this information is crucial to allow the physician to immediately adopt a procedural course that will best meet a patient's needs.

Arterial oxygen saturation ($S_aO_2$) is expressed as a percentage ratio of hemoglobin which is bound to oxygen (i.e., oxygenated hemoglobin ($HbO_2$ or "oxyhemoglobin")) to the total hemoglobin in the patient's blood (including both oxygenated ($HbO_2$) and non-oxygenated hemoglobin (Hb)), as represented by the following equation:

$$S_aO_2=([HbO_2]/([Hb]+[HbO_2]))\times 100\%$$

In a healthy patient, the $S_aO_2$ value is generally above 95% since blood traveling through the arteries has just passed through the lungs and has been oxygenated. As blood courses through the capillaries, however, oxygen is off-loaded into the tissues and carbon dioxide is on-loaded into the hemoglobin. Thus, the oxygen saturation levels in the capillaries ($S_cO_2$) is always lower than in the arteries. Once the blood has provided oxygen to the body tissue, the blood returns to the heart through the veins. Accordingly, the blood oxygen saturation levels in the veins is even lower still (i.e., about 75%).

Importantly, if the patient's arterial oxygen saturation level is too high or too low, the physician can take corrective action, such as reducing or increasing the amount of oxygen being administered to the patient, only after he or she learns of the incorrect saturation level. Proper management of arterial oxygen saturation is particularly important in neonates where $S_aO_2$ must be maintained high enough to support cell metabolism but low enough to avoid damaging oxygen-sensitive cells in the eye, which could cause impairment or complete loss of vision. Accordingly, in many applications, the continual provision of up-to-date information regarding the patient's pulse rate and oxygen saturation level is crucial to allow the physician to detect harmful physiological conditions before any observable physical manifestations of a substantial risk of injury arise. In settings such as operating rooms and in intensive care units, monitoring and recording these indicators of bodily functions is particularly important. For example, when an anesthetized patient undergoes surgery, it is generally the anesthesiologist's role to monitor the general condition of the patient while the surgeon proceeds with his tasks.

Typical techniques for measuring these characteristics include invasive procedures, such as using an inserted catheter to measure blood pressure and to extract periodic blood samples, or non-invasive techniques. Unfortunately, although invasive procedures are typically more accurate than non-invasive ones, they generally take several minutes to obtain results. These wasted minutes can be crucial in many medical situations as human tissue can begin to degenerate with lack of sufficient oxygen in just a few minutes. Non-invasive techniques are therefore generally preferred, not only because they avoid the painful insertion of needles or other instrumentation into a patient's body, but also because they offer a quicker response to changing physiological characteristics of the patient. Noninvasive techniques are also desirable when complex blood diagnostic equipment is not available, such as, for example, when a home health care provider performs a routine check-up in a patient's home.

The term "oximetry" has been adopted in the art to refer to noninvasive apparatus and methods for determining blood oxygen saturation levels. Conventional types of oximeters include finger oximeters, earlobe oximeters, and fetal oximeters. Conventional oximetry systems make use of the fact that the absorption characteristics of different blood components, namely, $HbO_2$ and Hb, differ depending on which wavelength of light (e.g., infrared or visible portions of the spectrum) is being used. Accordingly, typical noninvasive oximetric systems impinge at least both visible and infrared light upon a body part, such as a finger, and then estimate the $S_aO_2$ level using the relative proportions of visible and infrared light transmitted through or reflected by the body tissue. Undesirably, however, these conventional systems inherently include some inaccuracy, which increases to a substantial error for low (50–70%) $S_aO_2$ levels, due to, among other things, the inclusion of capillary blood as well as arterial blood in the light measurement readings.

In an effort to improve the accuracy of the $S_aO_2$ values obtained using two wavelengths of light, some systems have utilized the pulsatile component of the transmitted or reflected light beam to distinguish variations in the detected intensity of the light beam which are due to changes in blood components from other causes. This approach is generally referred to as pulse oximetry. Using the pulsatile signal modulating the light beams for obtaining an $S_aO_2$ estimate provides a significant improvement in accuracy over non-pulse oximetry systems.

"Pulsed oximeters" are therefore oximeters which measure the arterial component of the blood perfusion, to yield the arterial oxygen saturation ($S_aO_2$) level, using the pulsatile component of a light transmission signal. Companies have built special circuitry and developed algorithms to obtain good signal-to-noise ratios for this pulsatile measurement. These conventional circuits and algorithms typically yield a pulsatile factor (R) which is based in part on the ratio of the pulsatile component of light measurements at a red wavelength (eg., 600–800 nm) and at an infrared wavelength (eg., 800–1000 nm). More specifically, the pulsatile factor R is equal to a ratio of the pulsatile component divided by the steady-state component of light at the red wavelength to the pulsatile component divided by the steady-state component of light at the infrared wavelength, as shown by the equation:

$$R=(AC/DC)_{red}/(AC/DC)_{infrared}$$

The pulsatile factor R therefore properly corrects for variation in the power of the light sources and photodetectors comprising the measurement device. As will be discussed later, the ratio R does not, however, correct for the background tissue optics consisting of tissue thickness, tissue blood perfusion, light scattering, and boundary conditions such as bones and the air/tissue surface.

As explained above, traditional oximeters calibrate their pulsatile factor R measurement using non-invasive light transmission or reflection analysis as opposed to direct measurement of arterial $S_aO_2$ measured with catheters inserted in arterial vessels. More specifically, pulse oximeters monitor blood oxygen content by measuring the absorption of light in an arterialized vascular bed. Since oxyhemoglobin ($HbO_2$) and deoxyhemoglobin (Hb) absorb light differently, the relative concentration of each blood component and thus the $S_aO_2$ can be determined by measuring absorbed light at two different wavelengths. Pulse oximetry is now an established standard of care during anesthesia and in neonatal and adult critical care.

The basic design of conventional pulse oximeter probes includes both red and infrared light emitting diodes (LEDs) and a photodetector (or light transducer). These components are arranged so that the LEDs illuminate a particular section of arterialized tissue. The detector collects the light from the LEDs which has been transmitted through the tissue section but not absorbed by the skin, bone, blood and other physiologic absorbers. The steady-state (DC) and time-varying (AC) components of this signal are then used to calculate the fraction of the arterial blood which is oxygenated.

Pulse transmittance oximetry basically involves measurement of how the arterial blood in body tissue affects the intensity of light passing therethrough. More particularly, the volume of blood in the tissue is a function of the arterial pulse, with a greater volume present at systole and a lesser volume present at diastole. Because blood absorbs some of the light passing through the tissue, the intensity of the light emerging from the tissue is inversely proportional to the volume of blood in the tissue. Thus, the emergent light intensity will vary with the arterial pulse and can be used to indicate a patient's pulse rate. In addition, the absorption coefficient of $HbO_2$ is different from that of Hb for most wavelengths of light. For that reason, differences in the amount of light absorbed by the blood at two different wavelengths can be used to indicate the level of arterial oxygen saturation, $S_aO_2$. Thus, by measuring the amount of light transmitted through an earlobe or finger, for example, a pulse oximeter can be used to determine both the patient's pulse rate and arterial blood oxygen saturation.

The intensity of light transmitted through an earlobe, finger, or other body part is a function of the absorption coefficient of both "fixed" and "variable" components. Examples of "fixed" components include bone, tissue, skin, and hair. Examples of "variable" components include the volume of blood in the tissue. The intensity of light transmitted through the tissue is generally expressed as a function of time. It includes a baseline (or "DC") component, which varies slowly with time and represents the effect of the fixed components on the light transmission. It further includes a periodic pulsatile (or "AC") component, which varies more rapidly with time and represents the effect that changing tissue blood volume has on the light. Because the attenuation produced by the fixed tissue components does not contain information about pulse rate and arterial oxygen saturation, the pulsatile signal is of primary interest. In that regard, many of the transmittance oximetry techniques of the prior art eliminate the baseline component from the signal analyzed.

For example, U.S. Pat. No. 2,706,927 (Wood) measures light absorption at two wavelengths under a "bloodless" condition and a "normal" condition. In the bloodless condition, as much blood as possible is squeezed from the tissue being analyzed. Then, light at both wavelengths is transmitted through the tissue and absorption measurements made. These measurements indicate the effect that all non-blood tissue components have on the transmission of light through the tissue. When normal blood flow has been restored to the tissue, a second set of measurements is made that indicates the influence of both blood and non-blood components. The difference in light transmission measurements between the two conditions is then used to determine the average oxygen saturation of the tissue, including the effects of both arterial and venous blood. This process essentially eliminates the DC, non-blood component from the signal used to determine oxygen saturation.

For a number of reasons, however, the Wood method fails to provide the necessary accuracy. For example, a true bloodless condition cannot be obtained practically. In addition, efforts to obtain a bloodless condition, such as by squeezing the tissue, may result in a different light transmission path for the two conditions. In addition to problems with accuracy, the Wood approach is both inconvenient and time consuming and can cause damage to the tissue.

A more refined approach to pulse transmittance oximetry is disclosed in U.S. Pat. No. 4,086,915 (Kofsky et al.). The Kofsky et al. patent is of interest for two reasons. First, the technique of Kofsky et al. automatically eliminates the effect that fixed components in the tissue have on the light transmitted therethrough, avoiding the need to produce bloodless tissue. More particularly, as developed from the Beer-Lambert law of absorption for a clear medium with no light scattering, the derivatives of the intensity of the light transmitted through the tissue at two different wavelengths, when multiplied by predetermined pseudo-coefficients, can be used to determine oxygen saturation. Basic mathematics indicates that such derivatives are substantially independent of the DC component of the intensity, however the simple math does not hold for an optically turbid medium such as tissue with strong light scattering. The pseudo-coefficients are determined through measurements taken during a calibration procedure in which a patient first respires air having a normal oxygen content and, later, respires air of a reduced oxygen content. Unfortunately, this process is cumbersome.

Another reference addressed to pulse transmittance oximetry is U.S. Pat. No. 4,407,290 (Wilber). According to Wilber, light pulses produced by LEDs at two different wavelengths are applied to a body part, such as an earlobe. A sensor responds to the light transmitted through the earlobe, producing a signal for each wavelength having a DC and AC component resulting from the presence of constant and pulsatile absorptive components, respectively, in the earlobe. A normalization circuit employs feedback to scale both signals so that the DC, non-pulsatile components of each are equal and so that these offset voltages can be removed. Decoders separate the two signals, so controlled, into channels A and B where the DC component is removed from each. The remaining AC components of the signals are amplified and combined in a multiplexer prior to analog-to-digital (A/D) conversion. Oxygen saturation is then determined by a digital processor.

European Patent Application No. 83,304,939.8 (New, Jr. et al.) discloses yet another pulse transmittance oximeter. According to New, Jr. et al., two LEDs expose a body member, such as a finger, to light having red and infrared wavelengths, with each LED having a one-in-four duty cycle. A detector produces a signal in response to the light that is split into two channels. The one-in-four duty cycle allows negatively amplified noise signals to be integrated with positively amplified signals including the detector response and noise, thereby eliminating the effect of noise on the signal produced. The resultant signals include a substantially constant DC component and an AC component. To improve the accuracy of a subsequent analog-to-digital (A/D) conversion, a fixed DC value is subtracted from the signal prior to the conversion. This level is then added back in by a microprocessor after the conversion. Logarithmic analysis is avoided by the microprocessor because for each wavelength of light transmitted through the finger, a quotient of the AC component over the constant DC component is determined. The ratio of the two quotients is then determined and fitted to a curve of independently derived oxygen saturation levels. To compensate for the different transmission characteristics of different patient's fingers, an adjustable drive source for the LEDs is provided.

Pulsed oximetry has been successful as a trend detector to detect a sudden fall in $S_aO_2$ from the normal value of approx. 95%. However, pulsed oximetery has failed to prove accurate over a broad range of saturation levels. The subject-to-subject and tissue site-to-site variation in tissue blood perfusion is too great to allow a single calibration curve to relate R to $S_aO_2$ for all cases. Pulsed oximetry needs adaptive calibration to properly interpret R values based on pulsatile light transmission to yield accurate $S_aO_2$ values. There is a significant need for an oximeter with adaptive calibration.

SUMMARY OF THE INVENTION

One object of the present invention is to enable a method of determining an arterial blood oxygen saturation level that is accurate over various oxygen saturation levels.

Another object of the present invention is to enable a method of determining an arterial blood oxygen saturation level that is adaptively calibrated to give accurate blood oxygen saturation values over a range of oxygen saturation levels.

The present invention is an oximetry system that uses a plurality of sets of calibration curves, each containing a plurality of calibration curves, to permit accurate calibration of the system over a range of oxygen saturation levels.

According to the invention, an adaptively calibrated pulse oximeter uses the steady-state component of light transmission measurements to select a proper calibration curve. The selected calibration curve is then used to properly interpret the pulsatile factor obtained from the conventional measurement of the pulsatile component of the light signals to yield an accurate arterial blood oxygen saturation level determination.

In general, one method of determining an arterial oxygen saturation level according to this invention proceeds by using the DC components of light transmission measurements for both red and infrared light to determine a blood volume fraction/mixed blood oxygen saturation value pair. The unique pair is then used to select an appropriate calibration curve. Once the appropriate calibration curve has been selected, a pulsatile factor can then be used to determine the corresponding arterial blood oxygen saturation value.

More specifically, light measurements at the red and infrared wavelengths are taken with the probe in air (or some other standard medium). These calibration measurements are one-time measurements to allow correction for variation in the power of the light source and for variation in the responsivity of the detector. Subsequent measurements of the tissue are normalized by the calibration measurements. The normalized measurements are then used to determine the volume fraction of blood in the tissue and the mixed blood oxygen saturation value from a grid mapping. An appropriate calibration curve from among a plurality of calibration curves can then be selected using the blood volume fraction and the mixed blood oxygen saturation value.

According to one embodiment, a plurality of sets of calibration curves can also be provided. Each set of calibration curves includes a plurality of calibration curves relating the pulsatile factor to the arterial blood oxygen saturation level. The volume blood fraction and the mixed blood oxygen saturation value are used to select an appropriate calibration curve from among the plurality of calibration curves. Using the appropriate calibration curve, the pulsatile factor can be properly interpreted to yield an arterial blood oxygen saturation value. If the blood volume fraction or mixed blood oxygen saturation value of the patient's tissue site changes, the calibration will change accordingly to adaptively calibrate the determination of arterial blood oxygen saturation values.

BRIEF DESCRIPTION OF THE DRAWINGS

The foregoing objects, features, and advantages of the present invention will become more readily apparent from the following detailed description of multiple embodiments thereof, made with reference to the following figures, in which:

FIG. 1A is a schematic system level diagram illustrating an oximetry system for implementing the method of FIG. 1 according to another embodiment of the present invention.

FIG. 2 is a block flow diagram illustrating a basic algorithm for determining the arterial blood oxygen saturation level according to the method illustrated in FIG. 1.

FIG. 3 is a grid showing a relationship between light transport factors and blood volume fraction and mixed blood oxygen saturation values as used in the method illustrated in FIG. 1.

FIG. 4 is a graph showing a set of calibration curves for a given mixed blood oxygen saturation value for use in the method illustrated in FIG. 1.

FIGS. 5A and 5B are a listing of a calibration program for generating calibration curves for use in the method illustrated in FIG. 1.

FIG. 6 is a listing of a subroutine for calculating a pulsatile factor R for use in the calibration program of FIG. 5.

FIG. 7 is a graph showing calibration factors calculated for use in the method illustrated in FIG. 1.

FIGS. 8A and 8B are a program listing of a program for calculating calibration factors for use in the method illustrated in FIG. 1.

FIGS. 9A and 9B are a program listing of a computer program for generating the grid mapping of FIG. 3.

DETAILED DESCRIPTION

Figure 1:
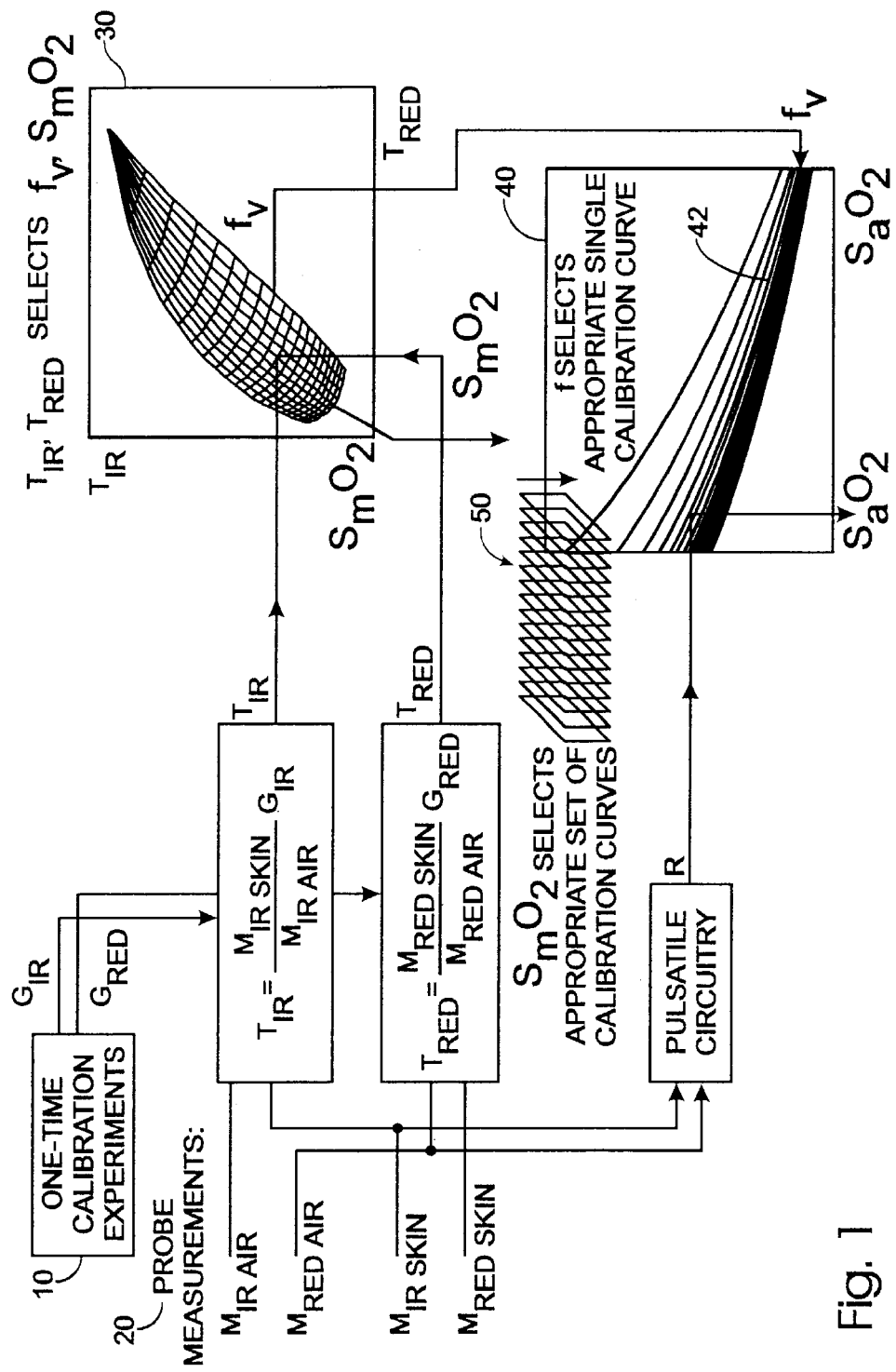
FIG. 1 is a schematic flow diagram illustrating a method of determining an arterial blood oxygen saturation level according to one embodiment of the present invention.

Like the prior art, the method and apparatus of this invention can be used to monitor blood oxygen saturation in the emergency room, in surgery, in intensive care, in the neonatal intensive care unit, monitoring the fetus during child birth, and in home use for monitoring peripheral vascular disease, among other uses. As noted previously, pulse oximeters measure the pulsatile change in transmission of light through a tissue due to the pulsatile change in tissue blood content caused by the beating heart. Such pulsatile measurements are generally made at two, wavelengths (red and infrared) which are combined to yield a pulsatile factor R that is directly related to the arterial blood oxygen saturation value, $S_aO_2$. Accordingly, by measuring R, the $S_aO_2$ can be determined.

Unfortunately, however, the calibration curve which maps an R value to an $S_aO_2$ value is not constant. The calibration curve of R versus $S_aO_2$ will vary from patient to patient and from tissue site to tissue site. The key factor underlying the failure of the prior art is the reliance of previous methods on the assumption of Beer's Law to describe light transport in tissue. Beer's Law would be appropriate if tissue were a cuvette of clear hemoglobin solution such that the tissue was transparent with no light scattering to cause optical turbidity. In such a case, the current calibration curves of R versus $S_aO_2$ would be accurate. Tissue turbidity due to light scattering, however, causes the light transport problem to become nonlinear, and the simple calculation of R consequently does not correct for the background tissue optics. The time-averaged blood content, both arterial and venous, influences the transport of light through the tissue and hence influences the calibration curve of R versus $S_aO_2$. Proper interpretation of the pulsatile (AC) component of light transmission to yield $S_aO_2$ requires a calibration that depends on the baseline (DC) component of light transmission.

In simple terms, consider dropping a drop of blood into a cup of milk and into a cup of milk plus coffee. In which cup would the color of the added blood be more pronounced? The color is more pronounced in the cup of milk than in the cup of milk plus coffee. In this analogy, the coffee mimics the time-averaged blood content, both arterial and venous, that influences the transport of light through the tissue. The added blood mimics the pulsatile increase in blood content of a tissue during the heart beat. To judge the amount of added blood by the color of blood in each cup one must account for the background optics (i.e., with or without coffee). The amount of coffee will vary the calibration curve required to deduce the amount of added blood from the color of blood in each cup. The judgment of the amount of added blood in the cup is analogous to deducing the $S_aO_2$ from a pulsatile oximetry measurement. In both, the calibration curve must be able to adapt to the background optics of the medium. This application calls this requirement "adaptive calibration."

Specifically, the calibration curve varies with changes in the optical properties (which determine an amount of light transport) through the tissue. For example, when the tissue's blood content or blood oxygen saturation level change, the absorption coefficient of the tissue also changes. Hence the light transport changes and the calibration also needs to be changed. In particular, fetal oximeters are more sensitive to such calibration problems than adult oximeters because fetal blood oxygen saturation levels can drop to much lower values than normal adult blood oxygen saturation. The calibration curve is more variable at lower blood oxygen saturation levels. The fetal oximeter, therefore, in particular, demands the proper choice of a calibration curve for each blood oxygen saturation level.

This invention employs findings regarding the influence of tissue optical properties and light transport on the calibration curve to provide an appropriate calibration curve in numerous physiological conditions. According to this invention, an adaptive calibration scheme is provided for selecting the proper calibration curve to interpret R to yield $S_aO_2$. The following definitions apply throughout this application:

| | |
|---|---|
| $DC_{red}$ = | steady-state transmitted signal at red wavelength (<800 nm) |
| $DC_{infrared}$ = | steady-state transmitted signal at infrared wavelength (>800 nm) |
| $f_v$ = | volume fraction of blood in tissue |
| $S_mO_2$ = | oxygen saturation due to mixture of arterial and venous blood |
| R = | factor based on pulsatile red and infrared signals |
| $S_aO_2$ = | oxygen saturation of arterial blood |

According to one embodiment of this invention, a method for adaptively-calibrating a pulsed oximeter is provided, which uses the steady-state or DC component of light transmission measurements to select an appropriate calibration curve. The selected calibration curve is then used to properly interpret the pulsatile factor (or "R value") obtained from a standard measurement of the pulsatile components to yield an accurate arterial blood oxygen saturation ($S_aO_2$) measurement.

FIG. 1 is a schematic flow diagram illustrating a method of determining an arterial blood oxygen saturation ($S_aO_2$)

level according to one embodiment of this invention. FIG. 1A is a system level view of an oximetry system for implementing the method of FIG. 1. Referring to FIG. 1, a method for determining the arterial blood oxygen saturation level, according to this embodiment, begins with a one-time calibration experiment 10. These experiments compare the DC component of light transmission measurements for both red and infrared wavelengths in air (or some other standard medium) with similar light transmission measurements taken when the probe is placed in contact with the desired tissue. In other words, two calibration measurements, one at each wavelength, are taken in air and compared with two calibration measurements, one at each wavelength, taken in the tissue. The two measurements in air are initial, one-time measurements that allow correction for variation in the power of the light source (e.g., light emitting diodes or laser diodes) and variation in the responsivity of the light detector (e.g., light transducer or photodiode). Subsequent measurements of the tissue (e.g., skin) are normalized using the air measurements.

A calibration factor G is also determined for each of the light wavelengths during the initial calibration process 10. The calibration factors are used to convert the ratio ($M_{skin}/M_{air}$) between subsequent light transmission measurements 20 of the probe in tissue ($M_{skin}$) and the previous air measurements ($M_{air}$) into a light transport factor, T, for each of the light wavelengths according to the following $$T_{ir} = G_{ir} \frac{M_{ir.skin}}{M_{ir.air}}$$

equations:
The red and infrared light transport factors ($T_{red}$ and $T_{ir}$, respectively) are in turn $$T_{red} = G_{red} \frac{M_{red.skin}}{M_{red.air}}$$

used to specify two unknowns, namely, the volume fraction of blood in the tissue ($f_v$) and the mixed blood oxygen saturation for the combined arterial and venous vasculature ($S_mO_2$) using a grid mapping 30.

Alternatively, however, the ratios of measurements in tissue to measurements in air ($M_{skin}/M_{air}$) can be directly mapped by a grid mapping 30 into values for the blood volume fraction and the mixed blood oxygen saturation, bypassing the need for calibration factors $G_{red}$ and $G_{ir}$ and transport factors $T_{red}$, $T_{ir}$ incorporating the calibration factors. Also, as mentioned previously, the measurements of air at red and infrared wavelengths can be substituted by measurements of some other standard material at those wavelengths. The ratios of the measurements of tissue to the measurements of the other standard material at red and infrared wavelengths is used to correct for source and photodector variations.

The grid mapping 30 is the result of calculations based on optical transport theory. In particular, optical transport theory is used to create a unique one-to-one mapping of $T_{red}$, $T_{ir}$ (or $M_{red.skin}/M_{red.air}$, $M_{ir.skin}/M_{ir.air}$) into $f_v$, $S_mO_2$. Once the blood volume fraction $f_v$ and mixed blood oxygen saturation $S_mO_2$ values have been obtained, the $S_mO_2$ value is used to select a set of calibration curves 40 relating R to $S_aO_2$ from among a plurality of sets calibration curves 50. The blood volume fraction $f_v$ is then used to select an appropriate calibration curve 42 from the selected set of calibration curves 40. Optical transport theory is also used to generate each of the calibration curves.

Once the appropriate calibration curve 42 has been selected, the pulsatile factor R can be properly interpreted to yield an accurate arterial blood oxygen saturation value $S_aO_2$. As a main benefit of this method, if the blood volume fraction $f_v$ or mixed blood oxygen saturation $S_mO_2$ of the patient's tissue site changes, the calibration will correspondingly change to allow the continued accurate determination of $S_aO_2$ values. As stated above, the ability of this method to readily adapt to changes in the tissue by continuously reselecting an appropriate calibration curve is called adaptive calibration. Adaptive calibration offers significant advantages over the prior art because it offers accuracy over a much wider range of blood oxygen saturation levels.

The optical properties of the tissue affect the transmission of light through the tissue. Interpretation of pulsatile signals and the choice of the appropriate calibration curve therefore also depend on the baseline optical properties of the tissue. To choose the appropriate calibration curve, therefore, the optical properties of the tissue must first be characterized. Important to this invention, it has been discovered that the non-pulsatile (steady-state or DC) measurements of transmitted light can be used to accomplish this task. As the tissue's blood content or blood oxygen saturation changes, the DC measurements ($DC_{red}$, $DC_{infrared}$) will also change, and the choice of calibration curve can be changed to provide accurate $S_aO_2$ approximations.

Fortunately, once recognized, the principles according to this invention are fairly straightforward to implement into an oximetry system that is similar in many respects to a conventional oximetry system. For instance, the basic circuitry and software for obtaining a pulsatile factor R with an optimal signal-to-noise can be retained. Additionally, the DC signals needed to calibrate the system are already measured in conventional systems and used to calculate the pulsatile R, although they are otherwise generally disregarded. The improved oximetry system according to this invention, therefore, need only be modified to permit adaptive calibration of the system. In other words, the data obtained from the current oximetry systems needs to be analyzed by an additional software module (or hardwired circuitry) to determine the appropriate calibration curve for interpretation of R to yield a predicted $S_aO_2$. This invention provides an algorithm for selecting the proper calibration curve based on the measured DC signals.

Referring to FIG. 1A, an oximetry system according to an embodiment of this invention includes an oximeter 100 configured to communicate with a data processor, such as a computer 120, through an analog to digital (A/D) converter 110. A display device, such as a monitor 130, can also be provided for viewing a visual representation of the physiological characteristics of a patient. According to this embodiment, the oximeter 100 includes a light source and a light transducer. The light source is capable of providing light of a first wavelength and a second wavelength (preferably red and infrared) to a patient's tissue (i.e., finger, ear lobe, fetal scalp skin, etc.). The light transducer communicates data regarding the transmission of light through (or reflection of light from) the tissue to the data processor 120 through the A/D converter 110. The data processor uses the light transmission data to determine an arterial blood oxygen saturation $S_aO_2$ level of the tissue using software adapted to cause the computer 120 to implement the method described herein. The software can be provided to the computer 120 on a computer readable medium such as a floppy disk, a CD ROM, etc., or via any other type of data transfer mechanism. A display device 130 is used to convey information regarding the $S_aO_2$ level to the attending physician to facilitate appropriate treatment.

FIG. 2 is a block diagram illustrating the basic algorithm for determining arterial blood oxygen saturation levels according to one embodiment of this invention. Referring to FIG. 2, although this basic algorithm utilizes the same calculation of the pulsatile factor R, based on the AC components of the light transmission measurements, as used in the prior art, it further adds the selection of an appropriate calibration curve. As indicated, the calibration curve is chosen based on the DC components of the light transmission measurements. The basic adaptive calibration algorithm according to this embodiment begins by using the DC components of light transmission measurements ($DC_{red}$, $DC_{infrared}$) to yield the light transport factors $T_{red}$, $T_{ir}$. The light transport factors $T_{red}$, $T_{ir}$ are then mapped into a unique blood volume fraction $f_v$, and a mixed blood oxygen saturation value $S_mO_2$. These values are representative of absorption and scattering characteristics of the tissue and can be used to adaptively select an appropriate R vs. $S_aO_2$ calibration curve.

An enlarged view of the grid mapping 30 of FIG. 1 is shown in FIG. 3. As noted above, the probe photodiode measurements on skin at both red and infrared light wavelengths $M_{red\ skin}$, $M_{ir\ skin}$ are normalized by dividing those measurements with the air calibration measurements $M_{red\ air}$, $M_{ir\ air}$. The normalized values ($M_{red\ skin}/M_{red\ air}$), ($M_{ir\ skin}/M_{ir\ air}$) are then multiplied by their respective calibration factor $G_{red}$, $G_{ir}$ to yield a red and an infrared light transport factor $T_{red}$, $T_{ir}$, respectively. These light transport factors $T_{red}$, $T_{ir}$ correspond directly to the steady-state components of the transmitted signals $DC_{red}$, $DC_{infrared}$ of FIG. 2.

Referring specifically to FIG. 3, the light transport factors $T_{red}$, $T_{ir}$ have a well-defined meaning in optical transport theory that depend on the blood volume fraction $f_v$ and mixed blood oxygen value $S_mO_2$ of the tissue. This relationship is represented by the grid mapping 30 of FIG. 3. As indicated by the grid mapping 30, a light transport factor pair $T_{red}$, $T_{ir}$ specifies a unique blood volume fraction and mixed blood oxygen value pair $f_v$, $S_mO_2$.

Once the $f_v$, $S_mO_2$ pair has been determined, the $S_mO_2$ value is used to select a specific set of calibration curves from among a plurality of sets of calibration curves, where each set of calibration curves includes a plurality of R vs. $S_aO_2$ calibration curves. Each calibration curve is for a given $f_v$ value. Accordingly, the $f_v$ value can then be used to select an appropriate one of the calibration curves, for the given light transmission properties of the tissue, from the set of calibration curves. The selected calibration curve allows the use of the pulsatile factor R to determine the arterial blood oxygen saturation level $S_aO_2$. Alternatively, however, the values of $f_v$ and $S_mO_2$ can jointly and directly select the appropriate calibration curve R versus $S_aO_2$ by means of an algorithm or lookup table.

A computational model is needed for predicting how the measured pulsatile ratio R will vary for changes in tissue blood content that affect absorption and for changes in tissue scattering properties. Absorption and scattering are the two optical properties that determine light transport properties. The following section provides a simple computational model for creating a calibration curve.

The optical properties of tissue are based on the absorption properties of water, bloodless tissue, oxygenated whole blood, and deoxygenated whole blood, and on the scattering properties of skin tissue and blood. These are summarized as follows:

$\mu_{a\ bloodless\ tissue} = 0.75\ \mu_{a\ water} + \mu_{a\ dry\ tissue\ absorption}$ $\mu_{a\ oxy\ whole\ blood} = (2.303)\in_{oxy\ Hb}(150\ \text{g/liter})/(66{,}500\ g\ Hb/\text{mole}) = 0.0052\in_{oxy\ Hb}$ $\mu_{a\ deoxy\ whole\ blood} = 0.0052\in_{deoxy\ Hb}$ where $\mu_{a\ water}$=spectrum (from Hale and Querry 1973)

$\mu_{a\ dry\ tissue\ absorption} \approx 85.3\ \exp(-(nm-154)/66.2)[cm^{-1}]$ (based on in vitro neonatal skin data by Saidi 1992)

$\in_{oxy\ Hb}$=Hb molar extinction coefficient spectrum (from Prahl 1998)

$\in_{deoxy\ Hb}$=Hb molar extinction coefficient spectrum (from Prahl 1998)

Some or all of the following references were helpful in obtaining the foregoing approximations:

G. M. Hall, M. R. Querry, "Optical constants of water in the 200 nm to 200 μm wavelength region," Appl. Opt., 12, 555–563 (1973). See the water spectrum on website http//omlc.ogi.edu/spectra/water/index.html.

S. A. Prahl 1998: http//omlc.ogi.edu/spectra/hemoglobin/index.html

I. S. Saidi 1992: "Transcutaneous optical measurement of hyperbilirubinemia in neonates," PhD Thesis, Rice University. Also, see the summary of skin optics on website http://omlc.ogi.edu/news/jan98/skinoptics.html. The constant offset 0.244 cm$^{-1}$ in Saidi's approximation has been removed since this is probably due to residual hemoglobin staining in the in vitro tissue samples measured.

It should be noted that the spectrum for $\mu_{a\ dry\ tissue\ absorption}$ is a crude approximation only. The above $\mu_{a\ dry\ tissue\ absorption}$ is consistent with the literature data for various reports on not quite bloodless aorta tissue samples (see for example http://omlc.ogi.edu/spectra/aorta/index.html). There appears to be a small amount of inevitable hemoglobin staining that dominates the absorption of in vitro tissues in the red-infrared spectral range of interest here. Although the above spectrum approximation is inaccurate at shorter wavelengths, this does not prevent its usefulness in the red-infrared range of interest in the primary embodiments of this invention.

The scattering properties of bloodless skin tissue and whole blood are very similar, at least with respect to their respective reduced scattering coefficients $\mu_s'$, which determines light diffusion. The net scattering of skin is calculated as follows:

$\mu_s' = f_v \mu_{s\ blood}' + (1-f_v)\mu_{s\ bloodless\ skin}'$ where $\mu_{s\ bloodless\ skin}'$=spectrum from Saidi et al. 1995

$\mu_{s\ blood}'$=spectrum from Roggan et al. 1999

One or more of the following references were helpful in obtaining the foregoing equation:

I. S. Saidi, S. L. Jacques, F. K. Tittel, "mie and Rayleigh modeling of visible light scattering neonatal skin," Applied Optics 34:7410–7418, 1995. Also see Jacques 1998: http://omlc.ogi.edu/

A. Roggan, M. Friebel, Klaus Doerschel, A. Hahn, G. Mueller, "Optical properties of circulating human blood in the wavelength range 400–2500 nm," J Biomedical Optica 4:36–46, 1999. Data for $\mu_s$ and g versus wavelength for 5% hematocrit blood. These data were used to calculate $\mu_s'$ for this report, as recorded in file "blood_scatterin.m".

A summary of the optical properties at the two wavelengths, 730 nm and 940 nm, used by the oximeter is given below in units of [cm$^{-1}$]:

| Tissue | $\mu_a$ 730 | $\mu_a$ 940 | $\mu_s$ '730 | $\mu_s$ '940 |
|---|---|---|---|---|
| oxy blood | 2.0280 | 6.3128 | 30.2715 | 23.5881 |
| deoxy blood | 5.7314 | 3.6059 | 30.2815 | 23.5881 |
| bloodless | 0.0276 | 0.2210 | 10.1402 | 6.9397 | where bloodless skin properties were based on:

| | $\mu_a$ 730 | $\mu_a$ 940 |
|---|---|---|
| water | 0.0179 | 0.2939 |
| dry dermis | 0.0142 | 0.0006 |

The computational module for calculating the R vs. $S_aO_2$ calibration curve will now be discussed. In developing this computational model, the parameters that can be varied by the user include:

The blood volume fraction, $f_v$, Describes the volume of blood per volume of tissue, a dimensionless fraction.

The arterial oxygen saturation, $S_aO_2$ Describes the oxygen saturation of the arterial blood supply, a value from 0 to 1 (or 0 to 100%).

The mixed blood oxygen saturation, $S_mO_2$ Describes the oxygen saturation of the combined venous and arterial blood supply, a value for 0 to $S_aO_2$ since $S_mO_2 \leq S_aO_2$.

The following description provides two alternative algorithmic implementations of the invention written in the MATLAB™ programming language. In a first embodiment, which follows the method illustrated in FIGS. 1, 2, and 3, a program called "calibrate.m" is used to generate the calibration curves for various $f_v$, $S_aO_2$, and $S_mO_2$ choices. A listing of the calibrate.m program is provided as FIG. 5. The program calls a subroutine called "calcR.m" which calculates the pulsatile factor R based on the equation:

R=calcR(optprops)

Where "optprops" is a vector containing the $\mu_s'$ of perfused skin, the $\mu_a$ of the mixed venous and arterial blood supply, and the $\mu_a$ of the arterial supply.

optprops=[musp, mua_mixed, mua_arterial]

The program "calibrate.m" begins by calling a subroutine called "tissueoptics.m" which loads the needed optical properties for all wavelengths from 250 to 1000 nm, then selects only the values for 730 and 940 nm. The optical properties are called oxy, deoxy, skin, musp_skin, and musp_bl, for the $\mu_a$ values of oxygenated blood, deoxygenated blood, and bloodless skin, and for the $\mu_s'$ values of bloodless skin and whole blood, respectively. For example, oxy(1) and oxy(2) are the $\mu_a$ oxy at 730 nm and 940 nm, respectively. All blood values are for 45% Hct blood.

The calibrate.m program then sequentially chooses a value for $f_v$ from 0.01 to 0.20:

for i=1:20
  fv=I*0.01; % choose series of blood volume fractions
And for each $f_v$, chooses a series of $S_aO_2$ values from 0 to 1.00 (0–100%):

for j=1:51
  SaO2=(j-1)/50; % choose series of $S_aO_2$ values

The $S_mO_2$ value is automatically chosen to be some fraction of the $S_aO_2$, for example:

SmO2=SaO2*0.80; % choose SmO2=fraction of SaO2
In the above case, the fraction was chosen to be 0.80 or 80% of the $S_aO_2$. Any fraction $0 \leq f \leq 1$ can be chosen. Physically, $S_mO_2$ cannot exceed $S_aO_2$.

Once the choices of $f_v$, $S_aO_2$, and $S_mO_2$ are made, the program proceeds to calculate the optical properties of the tissue:

mua_arterial=SaO2*oxy+(1-SaO2)*deoxy;

mua_mixed=$f_v$*(SmO2*oxy+(1-SmO2)*deoxy)+(1-fv) *skin;

musp=fv*musp_bl+(1-fv)*musp_skin;

Which are the absorption of the arterial blood supply, the absorption of the mixed venous and arterial blood supply, and the scattering of the tissue, respectively. These properties are assigned to the vector optprops.

Finally, the program calls the subroutine calcR.m:

R(j)=calcR(optprops);

The R value returned is assigned to the array element R(j) to facilitate later plotting. The $S_aO_2$ value is assigned to the array element SO2(j) for later plotting. After calculating R(j) and SO2(j) for all the $S_aO_2$ values, the curve is plotted. The next volume fraction $f_v$ is then computed and the process repeats. Accordingly, each calibration curve is for a separate $f_v$.

A listing of the calcR.m subroutine is provided in FIG. 6. The calcR.m subroutine will now be described in detail. The function assumes that the "effective source-detector distance" is d=0.55 cm, as was deduced from the diffusion theory analysis of the phantom experiments. The transport factor T [cm$^{-2}$] is calculated for the red and infrared wavelengths, i.e., for j=1:2. If a source power S[W] was specified, then the product S*T would equal the fluence F [W/cm$^2$] at the detector.

First, the absorption coefficient mua is assigned the value based on the mua_mixed value, which describes the blood content prior to a heart beat. The optical diffusion length D and the optical penetration depth delta are calculated. The transport factor T1 is calculated according to the equation:

T1(j)=exp(-d/delta)/(4*pi*D*d)

Next, a very small perturbation in the absorption coefficient mua is achieved by adding a small fraction (0.001) of the mua_arterial:

mua=mua_mixed(j)+0.00*mua_arterial(j)

Then the transport factor T2 is calculated:

T2(j)=exp(-d/delta)/(4*pi*D*d)

Finally, the pulsatile factor R is calculated in the standard fashion. Specifically, the "difference/mean" factors of the measurements before and after added arterial blood are determined, and the red/infrared ratio of these factors is then calculated according to the following equations:

A_730=(T2(1)-T1(1))*2/(T2(1)+T1(1)); % RED;

A_940=(T2(2)-T1(2))*2/(T2(2)+T1(2)); % INFRARED;

R=A_730/A_940

This R value is then returned to the calibrate.m program.

Using the R values, the program calibrate.m generates the R vs. $S_aO_2$ calibration curves for various values of $f_v$. FIG. 4 shows a set of calibration curves 40 for various blood volume fractions $f_v$=0.01 to 0.20 at a specified $S_mO_2$ level. To generate these curves, the value of $S_mO_2$ was set at 0.80*$S_aO_2$. Referring to FIG. 4, as the blood volume (represented by the fraction $f_v$) increases, the calibration curve moves downward toward lower R values. At first, increases in blood volume have a big effect. Later, at high blood contents, small additions of blood have less effect. The curves converge on a limiting calibration curve at very high blood contents. It should be noted that diffusion theory is not accurate at very high absorption coefficients, so the calibration curves at very high blood contents are not accurate. Fortunately, however, real skin perfusion does not usually range sufficiently high to violate the accuracy of diffusion theory.

It should be noted that the choice of $S_mO_2$ affects the calibration curves as well. The convention is followed that $S_mO_2$ is chosen to be a fraction ($0 \leq f \leq 1$) of the $S_aO_2$ level. The $S_mO_2$ value can only be less than or equal to the arterial oxygen saturation $S_aO_2$. Deoxygenation causes the calibration curves to fall slightly downward.

The effect of scattering on the calibration curve will now be discussed. First, consider a water solution in which hemoglobin has been added. The solution is clear. There is no light scattering. We can mimic the pulsatile blood content by simply adding a very small amount of hemoglobin to the solution. Measurements of light transmission before and after the addition constitute a "pulsatile" signal which allows a calculation of the pulsatile R value. The following programming statements replaced the diffusion theory statements in calcR.m to mimic transmission through a clear solution:

$$mua=mua\_mixed(j);$$

$$T1(j)=exp(-d*mua);$$

$$mua=mua\_mixed(j)+0.001*mua\_arterial(j)$$

$$T2(j)=exp(-d*mua)$$

Importantly, the calibration curves for the clear solution of hemoglobin (Hb), for all values of $f_v$=0.01 to 0.20 are identical. Without scattering, the R value is insensitive to blood volume fraction $f_v$. Scattering is therefore very important to the calibration curve of R vs. $S_aO_2$. It should be noted, however, that variation in the optical properties of the skin by a factor f that ranges from 0.5 to 2.0 has a negligible effect on the calibration curve. In other words, when the skin scattering properties range from ½ to twice normal, this 4-fold variation has negligible effect on the calibration curve, yet the curve is quite different from the clear solution of Hb. Since the scattering of neonatal skin is variable, dependent on the gestational development of collagen fibers in the neonate, the insensitivity of the pulsatile R value to variations in scattering in very important. As long as there is sufficient scattering to cause light to diffuse from source to detector, the calibration curve is otherwise insensitive to variations is $\mu_s'$.

Animal studies monitored the R measurements on skin with the spiral oximeter probe while measuring the $S_aO_2$ directly with an intravascular catheter probe. According to this research, the major determinant of the calibration curve is the blood volume fraction, $f_v$. The highest curve was obtained for a sheep which might have had a blood volume of 3%. The other animals showed values in the 6–8% range. The lowest curve for one pig, however, is below even the 20% blood volume fraction level. This demonstrates that another factor besides $f_v$ affects the calibration curve. That factor is mixed blood oxygen saturation $S_mO_2$.

As was discussed before, lowering the selected $S_mO_2$ value moves the calibration curves downward. The lowest pig curve from the animal experiments probably corresponds to a situation in which the $S_mO_2$ was low. In summary, the basic behavior of the animal data is mimicked by the calibrate.m program. A method of guessing what the choices of $f_v$ and $S_mO_2$ should be to specify the correct calibration curve will be addressed next.

As in the prior art, the two signals from the detector obtained during sequential illumination by the red LED and by the infrared LED are analyzed by special circuitry and software to determine the pulsatile factor R with a good signal-to-noise ratio. The raw signals also, however, have an average DC value that is related to the two parameters of interest, $f_v$ and $S_mO_2$. Referring back to FIG. 1, the basic steps of adaptive calibration according to one embodiment of this invention, include: (1) air calibration; (2) using the "grid.m" software program to allow $T_{ir}$, $T_{red}$ to uniquely specify $f_v$, $S_mO_2$; (3) using $S_mO_2$ to select a set of calibration curves; and (4) using $f_v$ to select a single calibration curve. These steps will now be described in further detail.

As shown in FIG. 1, two measurements, one each at the red and infrared wavelengths, are made first with the probe in air again when the probe is attached to the fetal scalp skin. Hence, four measurements are obtained: $M_{red\ air}$, $M_{ir\ air}$, $M_{red}$ $$\frac{M_{redskin}}{M_{redair}} = \frac{Sg1T_{redskin}Ag2D}{Sg3T_{redair}Ag4D} = \frac{g1g2}{g3g4T_{redair}}T_{redskin}$$

$skin$, $M_{ir\ skin}$. The ratio $M_{red\ skin}/M_{red\ air}$ is equivalent to:
Where:
- g1=factor describing how the power of the source is augmented by reflections from the mirrored surfaces of the spiral probe when in skin,
- g2=Factor describing how transmitted power couples to the detector through the tissue/epoxy/photodiode interfaces,
- g3=Factor describing how the power of the source is augmented by reflections from the mirrored surfaces of the spiral probe when in air,
- g4=Factor describing how transmitted power couples to the detector through the air/epoxy/photodiode interfaces,
- S=Power of the LED source [W],
- A=Area of collection at the detector [cm2],
- D=Detector responsivity [volts/W]

The normalization step (i.e., calculating a ratio between the light transmission measurements) cancels the influence of the factors S, A, and D. Hence, the effect of variations in the LED power or the photodetector responsibility are removed from the measurement. The above equation can alternatively be arranged:

$$R_{redskkin} = \frac{M_{redskin}}{M_{redair}} \frac{g_3g_4T_{redair}}{g_1g_2} = \frac{M_{redskin}}{M_{redair}}G_{red}$$

Where $G_{red}$ equals $T_{red\ air}\ g_3g_4/g_1g_2$. A similar expression yields $T_{ir\ skin}$ using $G_{ir}$.

The values of the factors $G_{red}$ and $G_{ir}$ must be experimentally determined. Such an experiment involves measuring $M_{air}$ for the red and infrared wavelengths. Once the air measurements are made, the probe is then inserted in a phantom tissue solution of known optical properties. In this manner, the value of the light transport factor T [cm$^{-2}$] can be calculated for the respective optical properties at the red (730 nm) and infrared (940 mm) wavelengths using the equation:

$$T = \frac{\exp(-d\sqrt{\mu_a/D})}{4\pi Dd}$$

Where $\mu_a$=absorption coefficient [cm$^{-1}$],

D=diffusion length [cm]=1/(3($\mu_a$+$\mu_s$')), $\mu_s$'=reduced scattering coefficient [cm$^{-1}$], d=the effective source-detector distance [cm].

For this embodiment, the experimental testing involved the testing of 24 spiral oximeter probes by taking a measurement in air followed by a measurement in 2% intralipid, for both the red and infrared wavelengths (i.e., 4 measurements). The value of light transport factors T for the red and infrared wavelengths were calculated based on the optical properties of the phantom. The values $G_{red}$ and $G_{ir}$ were then calculated using the expressions:

$$G_{red} = \frac{T_{red}}{(M_{redIL}/M_{redair})}$$

$$G_{ir} = \frac{T_{ir}}{(M_{irIL}/M_{irair})}$$

FIG. 7 shows the values of $G_{red}$ and $G_{ir}$ that were obtained using the above experiment. The analysis was accomplished using the MATLAB program "calcG.m," the listing for which is shown in FIG. 8. Ignoring probe #2, the mean values for G were 1.036±0.031 for red and infrared, respectively.

A program called "grid.m," a listing of which is shown in FIG. 9, is used to generate the grid that describes the relationship between $f_v$ and $S_mO_2$ and the values $T_{red}$ and $T_{ir}$. The program grid.m calls a subroutine function called "calcDC.m," listed in FIG. 9A, to begin the operation. The program grid.m assumes a background scattering value $\mu_s$' and uses the two parameters $S_mO_2$ and $f_v$ to specify the two optical properties $\mu_a$ and D which are used to calculate the transport factors $T_{red}$, $T_{ir}$. A series of values are used; i.e., $f_v$=0:0.01:0.20 and $S_mO_2$=0:0.1:1.0, to generate a set of $T_{red}$ and $T_{ir}$ values to yield the grid shown in FIG. 3. Referring to FIG. 3, the grid shows that as $f_v$ increases, both the $T_{red}$ and $T_{ir}$ drop to lower values. The grid also shows that as $S_mO_2$ increases, the $T_{red}$ increases while the $T_{ir}$ decreases. Measurements of $T_{red}$ and $T_{ir}$ uniquely map to an $f_v$, $S_mO_2$ pair. The $f_v$, $S_mO_2$ pair, in turn, will specify a unique R vs. $S_aO_2$ calibration curve. Accordingly, the $f_v$ and $S_mO_2$ specify the absorption ($\mu_a$) and scattering ($\mu_s$') properties of the tissue, as developed by the calibrate.m program, allowing the selection of the appropriate calibration curve. The selected calibration curve is then used to match the calculated pulsatile R value. from the conventional oximetry system with the $S_aO_2$ level.

Although the above description explains one approach and algorithm for accomplishing the objects of this invention, it should be noted that many different approaches and algorithms are within the contemplation of this invention. An alternative and preferred algorithm will now be described. According to a presently preferred algorithm, the time-averaged DC measurements of a standard calibration material, such as air, water, or some other standard medium, ($M_{std.red}$, $M_{std.ir}$) and the DC measurements of tissue ($M_{tissue.red}$, $M_{tissue.ir}$), are derived from an oximeter to yield normalized light measurement values:

mT$_{red}$=M$_{tissue.red}$/M$_{std.red}$ mT$_{ir}$=M$_{tissue.ir}$/M$_{std.ir}$ Also, a pulsatile factor (R value) is obtained from the pulsatile AC component of the oximeter measurements and is called mR. These three values mT$_{red}$, mT$_{ir}$, and mR are determined and passed to a subroutine getSaO2([mTred, mTir, mR]) to yield a prediction of the arterial oxygen saturation $S_aO_2$ which is accurate despite variations in the blood volume fraction, $f_v$, or the mixed blood oxygen saturation, $S_mO_2$. The program getSaO2( ), written in the MATLAB™ programming language, is listed here:

```
function SaO2 = getSaO2 ( [mTred, mTir, mR] )
%%%
% Returns the arterial oxygen saturation SaO2
% given the normalized measurements:
%       mTred    = M_tissue_red/M_std_red
%       mTir     = M_tissue_ir/M_std_ir
%%%
[fv, SmO2]   = grid(mTred, mTir) %
[C0 C1 C2]   = calibcurve ( [fv, SmO2] ) %
SaO2         = C0 + C1*mR + C2*mR^2;       % FINAL ANSWER
```

The function getSaO2( ) uses the normalized light measurement data [mTred, mTir] to specify the blood volume fraction and mixed blood oxygen saturation values [fv, SmO2], which in turn specify a calibration curve for $S_aO_2$ as a function of R that has been summarized as a second-order polynomial. The polynomial is used to convert the pulsatile measurement mR into a predicted $S_aO_2$. The final answer is the predicted $S_aO_2$.

The above function getSaO2( ) is the complete master routine which handles the direct feed of measurement data from an oximeter via a master program. The details of the functions grid( ) and calibcurve( ) are presented in the following paragraphs. Both grid( ) and calibcurve( ) use two transport functions mTred( ) and mTir( ). First, a description of how mTred( ) and mTir( ) are prepared is provided.

In a one-time set of calibration experiments using a particular oximeter probe design, such as a probe designed for the adult finger or a probe designed for the skin of the fetal head during birth, two light transport factors $T_{red}(\mu_a, \mu_s')$ and $T_{ir}(\mu_a, \mu_s')$ are specified by measurements in a series of calibrated phantoms of known optical properties consisting of various absorption coefficients ($\mu_a$) and reduced scattering coefficients ($\mu_s$'). at the red and infrared wavelengths. These transport factors are similar to the transport factors predicted by optical diffusion theory or other transport theories found in the scientific literature but further include the influence of the specific probe geometry. They are computed from the measured values of the phantoms:

$T_{red}(\mu_a, \mu_s')$=$M_{phantom.red}(\mu_a, \mu_s')$/$M_{std.red}(\mu_a, \mu_s')$ $T_{ir}(\mu_a, \mu_s')$=$M_{phantom.ir}(\mu_a, \mu_s')$/$M_{std.ir}(\mu_a, \mu_s')$ These calibration experiment results are summarized by two functions, Tred(mua, musp) and Tir(mua, musp), where mua=$\mu_a$ and musp=$\mu_s$', which receive the arguments ($\mu_a$, $\mu_s$') and return the expected values of ($M_{phantom.red}$/$M_{std.red}$) and ($M_{phantom.ir}$/$M_{std.ir}$). For example, implementations of Tred( ) and Tir( ) for a particular type of oximeter probe using water as the standard material are shown below as two MATLAB™ programs:

```
function mTred = Tred (mua, musp)
% Returns mTred = M_red/M_std_red
% given tissue absorption (mua) and scattering (musp)
% In this case, the standard was water.
m1 = 0.7443;
m2 = 2.5435;
m3 = 0.2612;
m4 = 29.7706;
const = m1*exp(-musp/m2) + m3*exp(-musp/m4) ;
d     = 0.2904; % [cm] apparent source-detector distance
a     = 0.4779; % [cm^-1] an apparent background mua
D     = 1/3./((a + mua) + musp) ;
mueff = sqrt((a + mua) ./D) ;
mTred = const*exp(-mueff*d) ./ (4*pi*D*d) ;   % FINAL ANSWER
function mTir = Tir (mua, musp)
% Returns mTir = M_ir/M_std_ir
% given tissue absorption (mua) and scattering (musp)
% In this case, the standard was water.
m1 = 0.6664;
m2 = 2.5695;
m3 = 0.4168;
m4 = 27.6357;
const = m1*exp(-musp/m2) + m3*exp(-musp/m4) ;
d     = 0.2825; % [cm] apparent source-detector distance
a     = 0.3143; % [cm^-1] an apparent background mua
D     = 1/3./((a + mua) + musp) ;
mueff = sqrt((a + mua) ./D) ;
mTir = const*exp(-mueff*d) ./ (4*pi*D*d) ;   % FINAL ANSWER
```

The function grid( ) uses Tred( ) and Tir( ) in conjunction with an optical properties library which is loaded by the command "load tissueoptics". This library includes the spectral optical absorption properties of oxy-hemoglobin in whole blood (oxy), deoxy-hemoglobin in whole blood (deoxy), and bloodless tissue (mua_tissue), and the optical scattering properties of the tissue (musp_tissue) and of blood (musp_blood). The absorption properties of bloodless tissue are based on the absorption properties of water and the non-aqueous components of bloodless tissue. This library is prepared from values in the scientific literature. For example, for skin the library is specified by values from the scientific literature as follows:

```
%%%
% Created by the command "load tissueoptics"
% In this case, tissue is skin, red = 730 nm, infrared = 900
nm
%%%
oxy         = [2.03, 6.31] ;      % [mua_red, mua_ir], as [cm^-1]
deoxy       = [5.73, 3.61] ;      % [mua_red, mua_ir]
mua_tissue  = [0.0276, 0.221] ;   % [mua_red, mua_ir]
musp_tissue = [10.2, 6.94] ;      % [musp_red, musp_ir]
musp_blood  = [30.3, 23.6] ;      % [musp_red, musp_ir]
```

The subroutine grid( ) uses a standard minimization algorithm, called fmins( ) in MATLAB™, and an error evaluation function fvSmO2grid( ) to directly calculate $f_v$ and $S_mO_2$ based on the measurements [mTred, mTir]:

[fv, SmO2]=grid([mTred, mTir])

An implementation of the functions grid( ) and fvSmO2grid( ) are shown below in MATLAB™ format:

```
%%%
% function [fv SmO2] = grid(mTred, mTir)
%       where
%           mTred = mua_red/mua_std_red
%           mTir  = mua_ir/mua_std_ir.
% Program returns the values for blood volume fraction (fv)
% and mixed blood oxygen saturation (SmO2) .
%   Uses the functions Tred (mua, musp) and Tir (mua, musp)
functions
% determined experimentally in phantoms of known optical
properties.
% The values mua_red and mua_ir refer to DC measurements on
tissues
% and mua_std_red and mua_std_ir refer to measurements
% of the standard.
%%%
global Data      % Links Data to the subroutine grid( [fv SmO2] ).
                 % The array Data is described below.
load tissueoptics;    % Loads the optical properties as two
numbers each,
                 % [value for red, value for ir] for the
following:
                 % oxy (1:2), deoxy (1:2), musp_bl (1:2),
                 % mua_tissue (1:2), and musp_tissue (1:2)
                 % which are defined below:
Data = zeros (6,2) ;  % Establish size of array.
Data (1,1:2) = [mTred, mTir] ;   % normalized tissue measurements
Data (2,1:2) = oxy;              % mua of oxy whole blood        (45%
hematocrit)
Data (3,1:2) = deoxy;            % mua of whole deoxy blood      (45%
hematocrit)
Data (4,1:2) = musp_bl;          % musp of whole blood           (45%
hematocrit)
Data (5,1:2) = mua_tissue;   % mua of bloodless tissue
Data (6,1:2) = musp_tissue;  % musp of bloodless tissue
% Call the minimization subroutine, fmins (), that finds [fv
SmO2]
% based on [mTred mTir] .
% An initial guess is provided to fmins () which then
iteratively
```

-continued

```
% uses fvSmO2grid ( [fv SmO2] ) to determine the error in the
current
% choice of [fv SmO2] then improves its choice of [fv SmO2].
% When the error is minimized, then [fv SmO2] is returned.
fv = 0.10;          % an initial guess
SmO2 = 0.70;        % an initial guess
Start [fv SmO2] ;
[fv SmO2] = fmins ('fvSmO2grid', start);    % FINAL ANSWER
returned
function err = fvSmO2grid (choice)
%%%
% This subroutine uses a choice for [fv SmO2] = choice
provided
% by the standard MATLAB minimization program called fmins ()
% to predict values of pT = M/M_std for red and infrared
% wavelengths. These predictions are compared with the
% actual measurements which are passed to this subroutine
from
% the program grid () via the global variable Data (1, 1:2) =
% [mTred mTir] . The sum of the squared differences between
% [mTred mTir] and [pTred pTir] constitutes the "error"
% between measurement and prediction, and this error is
% returned to the calling function fmins () . The routine
fmins ()
% iteratively calls this subroutine and improves its choice
% for [fv SmO2] . Eventually the error is minimized and
fmins ()
% stops iterating and returns the best estimate for [fv SmO2]
to
% the main program.
%%%
global Data    % links Data from program grid () to this
subroutine
%%% Choices being checked:
       fv           = choice (1) ;
       SmO2         = choice (2) ;
%%%    Data provided via global variable Data (6,2) :
       mT           = Data (1,1:2) ;   % [mTred, mTir]
       oxy          = Data (2,1:2) ;   % mua of oxy whole blood
       deoxy        = Data (3,1:2) ;   % mua of deoxy whole blood
       musp_bl      = Data (4,1:2) ;   % musp of whole blood
       mua_tissue   = Data (5,1:2) ;   % mua of bloodless tissue
       musp_tissue  = Data (6,1:2) ;   % musp of tissue
%%%       Linearly mix optical components to yield mua and musp:
       mua     = fv* (SmO2*oxy + (1-SmO2) *deoxy) + (1-
fv)*mua_tissue;
       musp    = fv*musp_bl + (1-fv) *musp_tissue;
%%%       Predict measurements:
       pTred   = Tred (mua (1), musp (1)) ;
       pTir    = Tir (mua (2), musp (2)) ;
%%%       Sum squared differences between measurements and
% predictions for return to fmins () :
       err     = (pTred - mT (1)) ^2 + (pTir - mT (2)) ^2; % FINAL
ANSWER
```

Once the $f_v$ and $S_mO_2$ of the tissue are specified, the function calibcurve( ) is used to return a calibration curve for $S_aO_2$ versus R:

[C0, C1, C2]=calibcurve([fv, SmO2])

where $S_aO_2$ is represented by a second order polynomial of the form:

SaO2=C0+C1*R+C2*R^2

By stepping through a set of $S_aO_2$ values and using the $f_v$ and $S_mO_2$ values, a series of $\mu_a$ and $\mu_s'$ values for the blood perfused tissue are generated for the red and infrared wavelengths. These values are sent to the subroutines Tred(mua, musp) and Tir(mua, musp) to return predictions of time-averaged measurements ($M_{tissue.red}/M_{std.red}$) and ($M_{tissue.ir}/M_{std.ir}$). Then, an incremental amount of arterial blood is added to the computer-simulated tissue by increasing the $\mu_a$ and $\mu_s'$ values as if a 0.1% increase in blood volume fraction had occurred due to the added arterial blood. Again, the subroutines Tred(mua, musp) and Tir(mua, musp) are used to return predictions of the pulsatile measurements $M_{tissue.red}/M_{std.red}$ and $M_{tissue.ir}/M_{std.ir}$ acquired at the peak in blood volume fraction due to expanded arterial volume. Then the pulsatile R value is calculated according to the equation:

$$R=[(M_{tissue.red}/M_{std.red})/(M_{tissue.red}/M_{std.red})]/[(M_{tissue.ir}/M_{std.ir})/(M_{tissue.ir}/M_{std.ir})]$$

By repeating the above for each choice of $S_aO_2$, one generates the conventional calibration curve R versus $S_aO_2$, which is inverted to read as $S_aO_2$ versus R. A second-order polynomial is fit to this inverted calibration curve such that:

$$SaO2 = C0 + C1*R + C2*R^2$$

This polynomial allows immediate evaluation of a measured pulsatile mR value from the oximeter to yield an arterial oxygen saturation value $S_aO_2$:

$$SaO2 = C0 + C1*mR + C2*mR^2$$

This value SaO2 is the final answer of the algorithm.

The subroutine calibcurve( ) is listed below. The subroutine uses the subroutine calcR(optprops) to compute the expected pulsatile R for a specified set of optical properties specified by the argument optprops which holds the optical properties of the tissue with mixed arterial/venous blood and of arterial blood. For each of 51 choices of SaO2, 51 values of R are generated using calcR( ). Then a second-order polynomial is fitted to the relation of SaO2(1:51) versus R(1:51) to yield the coefficients [C0, C1, C2].

```
function [c2 c1 c0] = calibcurve ( [fv SmO2] )
%%%%%
% Given [fv, SmO2] , this program
% returns the answer [c2 c1 c0]
%       where SaO2 = c0 + c1*R + c2*R^2
%       and R is the pulsatile factor from a pulsed oximeter.
% Program creates the calibration curve R versus SaO2
% then fits the program with a second-order polynomial.
%   Uses      subroutine calcR () and optical properties array
Data (6,2) .
%%%%
global Data
% Data provided:
mT              = Data (1, :) ;    % NOT USED HERE
oxy             = Data (2, :) ;    % mua of oxy whole blood
deoxy           = Data (3, :) ;    % mua of deoxy whole blood
musp_bl         = Data (4, :) ;    % musp of whole blood
mua_tissue      = Data (5, :) ;    % mua of tissue
musp_tissue     = Data (6, :) ;    % musp of tissue
% Cycle through series of SaO2 values = 0 to 1.00
for j = 1:51
    SaO2 (j)        = (j-1)/50;
    mua_arterial    = SaO2 (j) *oxy + (1-SaO2 (j)) *deoxy;
    mua_mixed       = fv*( SmO2*oxy +
                      (1-SmO2) *deoxy ) + (1-
fv)*mua_tissue;
    musp            = fv*musp_bl + (1-fv) *musp_skin;
    optprops        = [musp, mua_mixed, mua_arterial] ;
    R (j)           = calcR (optprops);  % Calculate pulsatile R
value
end
[c2 c1 c0] = polyfit(R, SaO2, 2) ; % where SaO2 = c0 + c1*R +
c2*R^2
                                   % FINAL ANSWER
function R = calcR ( [fv, SmO2, SaO2] )
%%%
% calcR.m
% Returns pulsatile value R = calcR (optprops) ,
%     where optprops = [musp_red musp_ir mua_mixed_red
mua_mixed_ir
%                                        mua_arterial_red
                                         mua_arterial_ir]
%%%
musp            = optprops (1:2) ;
mua_mixed       = optprops (3:4) ;
mua_arterial    = optprops (5:6) ;
%%%
% For time-averaged blood content
%%%
mua (1) = mua_mixed (1) ;
mua (2) = mua_mixed (2) ;
```

```
T1 (1) = Tred (mua (1), musp (1)) ; % red
T1 (2) = Tir (mua (2), musp (2)) ; % infrared
%%%
% For peak arterial blood content = a 0.1% increment in blood
content
%%%
mua (1) = mua_mixed (1) + 0.001*mua_arterial (1) ;
mua (2) = mua_mixed (2) + 0.001*mua_arterial (2) ;
T2 (1) = Tred (mua (1) , musp (1)) ; % red
T2 (2) = Tir (mua (2) , musp (2)) ; % infrared
%%%
% Calculate pulsatile R value
%%%
A_red= (T2 (1) - T1 (1)) /T1 (1) ; % RED
A_ir = (T2 (2) - T1 (2)) /T1 (2) ; % INFRARED
R = A_red/A_ir;       % FINAL ANSWER
```

Finally, the coefficients [C0, C1, and C2] can be used to interpret the measured pulsatile factor mR received from the oximeter as described above.

Various improvements to the foregoing embodiments have been developed since the filing of the original disclosure. The original disclosure describes the use of a steady-state component of light transmission measurements at two wavelengths through a tissue to select a proper calibration curve for interpretation of the pulsatile component of the light transmission. The selected calibration curve allows pulsatile measurements to specify the arterial blood oxygen saturation.

The standard pulsed oximetry of conventional medical practice relies on a single average calibration based on measurements on a subject population. The baseline level of nonpulsatile blood content, however, both arterial and venous, in a tissue can vary significantly from patient to patient, and even from site to site on any given patient. Conventional pulsed oximetry is therefore not calibrated for a particular patient or tissue site, but rather for an average patient. The principles of the invention described above provide dynamic adaptive calibration for standard pulsed oximetry, which can adjust to any variation in the amount of mixed arterial and venous blood volumes in a tissue.

Improvements extending the above-described principles of the invention enable oximetry to be conducted on tissues that have complex geometry and composition. For example, a surgically-implanted oximetry device (e.g., a light source and a detector) might enable performance of pulsed oximetry on blood vessels that carry blood to and from the brain so as to assess the oxygen utilization by the brain and the ability of cardiac output to meet the oxygen requirements of the brain. An implanted oximetry device encounters a complex geometry with a surrounding tissue, a vessel wall, and an inner lumen filled with blood. Furthermore, the optical properties of the surrounding tissue may vary. The thickness of the vessel wall may also vary from patient to patient and the size of the inner lumen may vary.

Given these additional variables, it is desirable for an embodiment of the invention to conduct more measurements in order to specify the oxygen saturation. To accomplish this, it is desirable to expand the number of measurements that are included in the oximetry method to provide accurate measurements in more complex tissues.

Figure 10A:
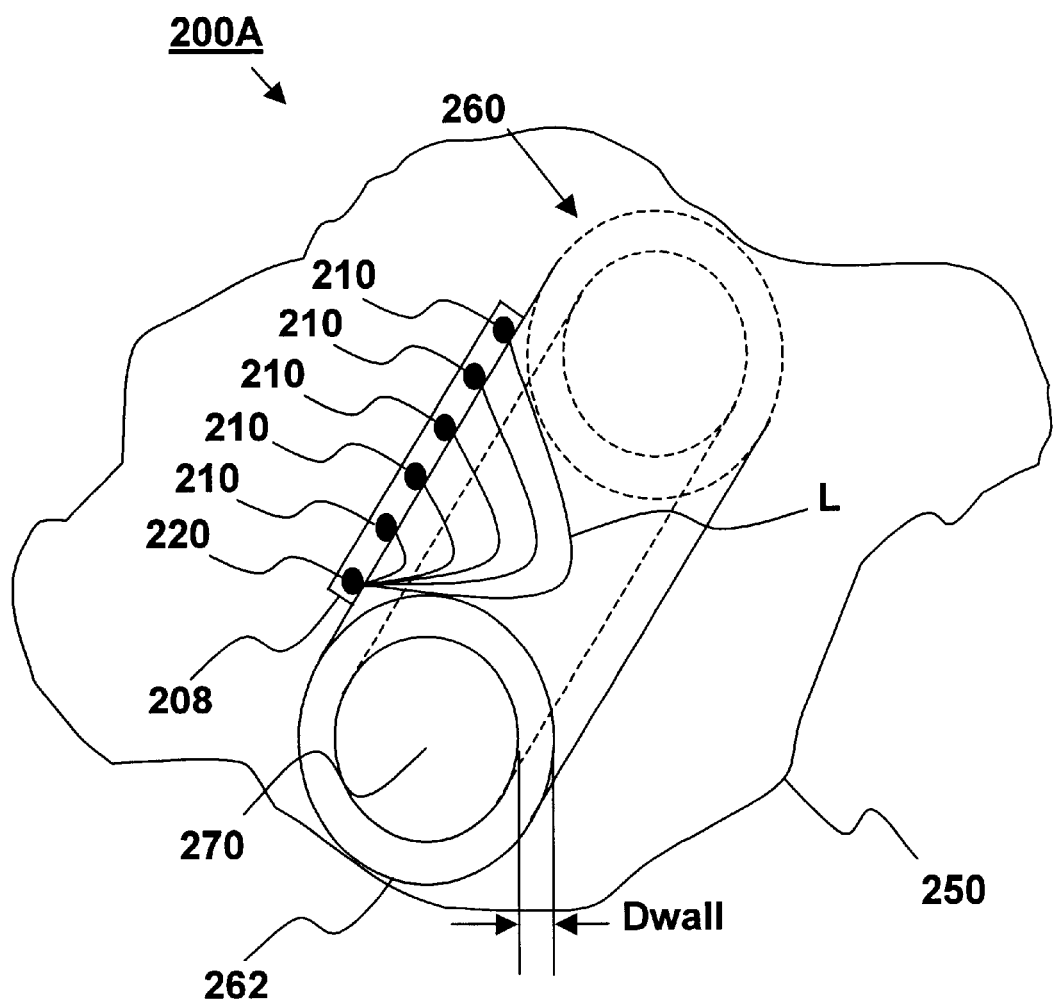
FIG. 10A is a schematic diagram illustrating use of an oximetry device with different source-detector separations according to an extended embodiment.
Figure 10B:
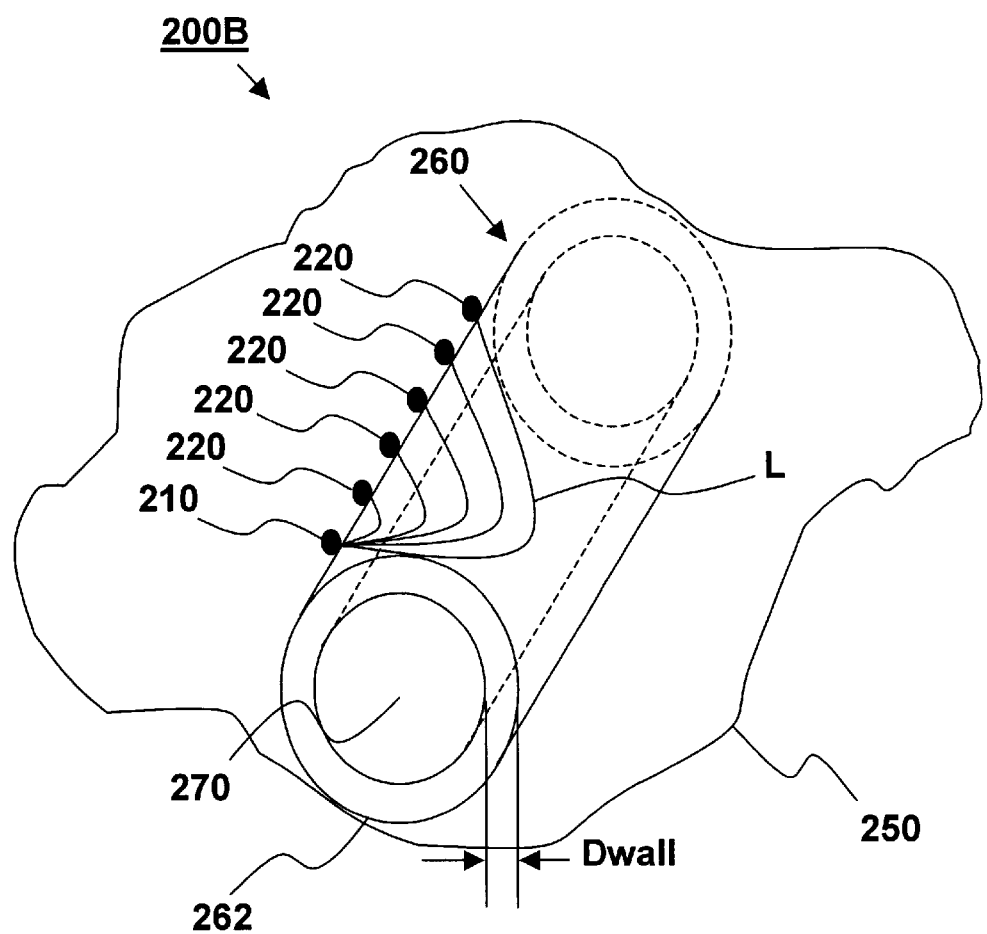
FIG. 10B is a schematic diagram illustrating use of another oximetry device having a plurality of source-detector separations according to another extended embodiment of the invention.

FIGS. 10A and 10B are schematic diagrams illustrating use of oximetry devices 200A, 200B to detect blood oxygen saturation of a sample tissue 250. Referring to FIGS. 10A and 10B, according to these improved embodiments, for example, a number of light sources 210 and/or a number of detectors 220 in an oximetry device 200A, 200B are used to provide a range of source-detector separations. The light sources 210 (and/or the detectors 220) can be arranged, for instance, in an array 208. The circuitry that actuates the light sources 210 and circuitry that processes the output signals from the detectors 220, are not shown in FIGS. 10A and 10B, but can be routinely designed by those skilled in the art.

Each measurement at a different source-detector separation involves a different ensemble of path lengths L through the tissue 250 for the collected photons. Consequently, each measurement is unique and independent. Small source-detector separations probe the vessel wall 262, while large source-detector separations probe the blood volume 270 within the vessel 260. The oximetry calibration algorithm is preferably adapted to utilize the additional information obtained from these measurements and thereby yield an accurate adaptive calibration for use with pulsatile information.

Referring back to FIG. 1, according to the principles of the invention described previously, an appropriate $f_v$-$S_mO_2$ grid 30 can be selected using measurements of $T_{IR}$ and $T_{RED}$ to yield values of $f_v$ and $S_mO_2$. The $S_mO_2$ value can then be used to select a set 40 of calibration curves from a group of sets 50, and the $f_v$ value can be used to select a calibration curve 42 from the selected set 40.

According to the improved embodiments of the invention shown in FIGS. 10A and 10B, additional measurements at several source-detector separations yield a set of measurements ($T_{IR1}$, $T_{RED1}$, $T_{IR2}$, $T_{RED2}$, $T_{IR3}$, $T_{RED3}$, ...) that specify the vessel wall thickness (Dwall), the average path length (Lblood) of the ensemble of collected photons that pass through the vessel blood volume 270, and the optical properties (mua, musp) of the averaged surrounding tissue 250, vessel wall 262, and blood-filled vessel lumen 270 that are associated with the nonpulsatile component of the light transmission. The optical properties specified are the absorption coefficient mua [cm$^{-1}$] and the reduced scattering coefficient musp [cm$^{-1}$].

The combination of parameters (Dwall, Lblood, mua, musp) is used to specify a calibration curve, similar to the calibration curve 42 of the original embodiments, that allows the pulsatile component of transmission to specify the arterial oxygen saturation ($S_aO_2$). At least five independent measurements are preferably used to specify the five variables (Dwall, Lblood, mua, musp, $S_aO_2$).

In a variation of the foregoing embodiments, the actual position of certain sources and detectors is varied. The position information, rather than just the source-detector separation information, is then used in specifying the parameters that are in turn used to specify the calibration curve required to interpret pulsatile measurements to yield an arterial blood oxygen saturation ($S_aO_2$) value.

Figure 11:
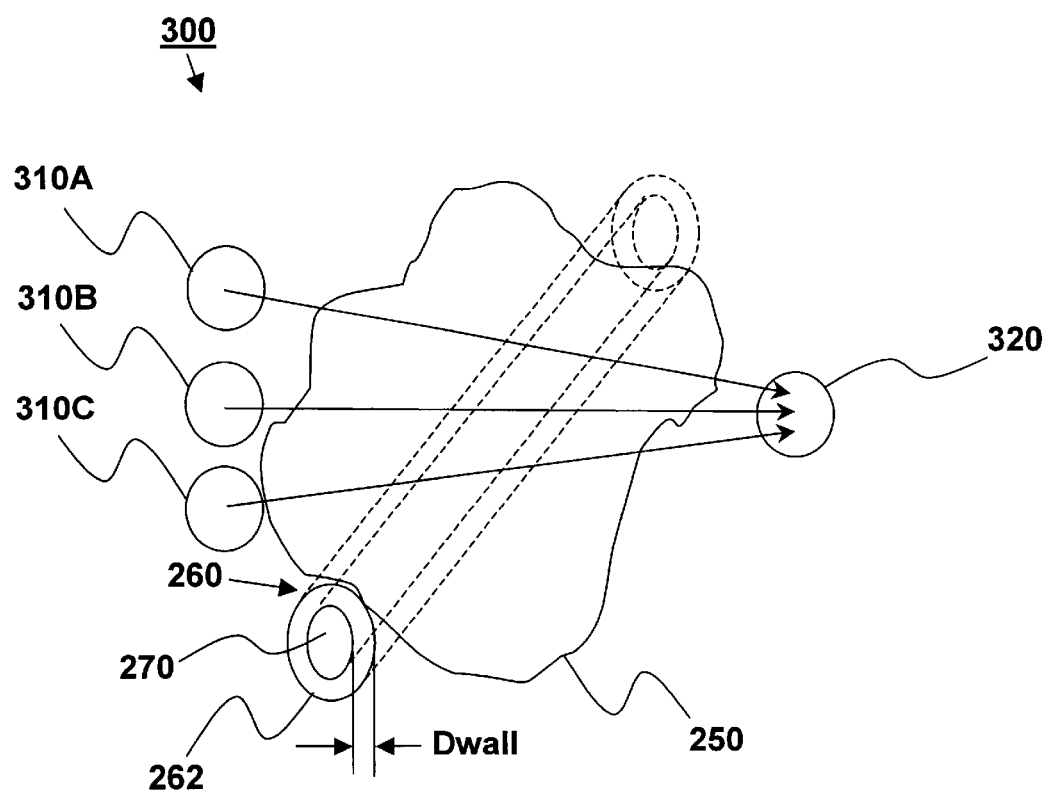
FIG. 11 is a schematic diagram illustrating use of an oximetry device using multiple light sources of different wavelengths according to yet another extended embodiment of the invention.

In another improved embodiment of the invention, illustrated in FIG. 11, additional measurements are preferably obtained using more than two light sources 310A, 310B, 310C of different wavelengths in the visible to near-infrared wavelength range. Shorter wavelengths probe the vessel wall 260 and longer wavelengths probe into the blood-filled vessel lumen 270. Inclusion of more light sources provides additional measurements. As with the previous improvement, a set of transmission measurements ($T_{wavelength1}$, $T_{wavelength2}$, $T_{wavelength3}$, $T_{wavelength4}$, $T_{wavelength5}$, ...) are obtained. At least five independent measurements are preferably obtained to determine values for the five variables (Dwall, Lblood, mua, musp, $S_aO_2$). Most preferably, both a plurality of wavelengths and a plurality of source-detector separations and positions can be implemented.

Figure 12:
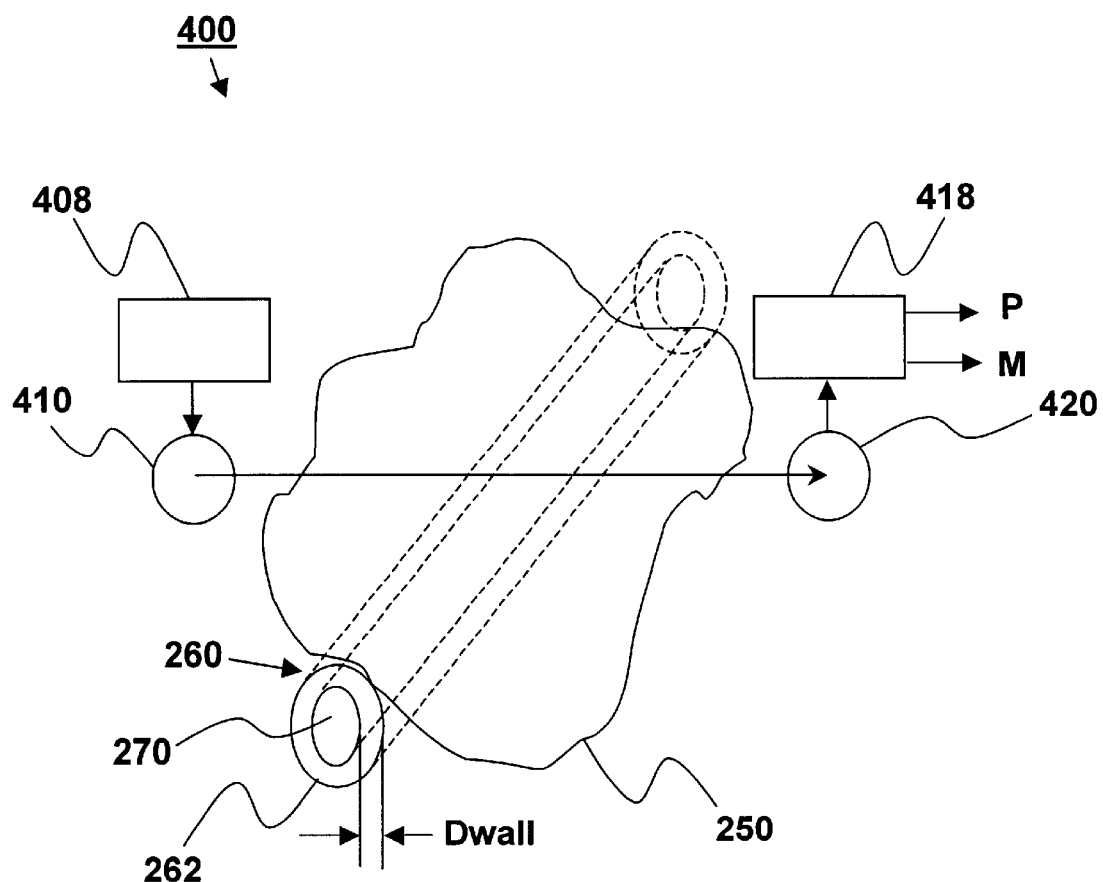
FIG. 12 is a schematic diagram illustrating use of an oximetry device using a modulated light source to obtain measurements for determining a blood oxygen saturation level according to a further extended embodiment of the present invention.

In yet another improvement, illustrated schematically in FIG. 12, additional measurements are achieved using a modulator 408 (e.g., preferably using amplitude modulation, but alternatively using frequency or phase modulation) to modulate the light source 410 at various high frequencies, such as between 50 kHz and 1 GHz. A demodulator 418 measures the phase P and modulation M of the transmitted light received at the detector 420. The measurements at different frequencies of modulation involve different path lengths for collected photons and therefore probe different proportions of the surrounding tissue 250, vessel wall 262, and blood-filled lumen 270. Multiple independent measurements of P and M at various frequencies ($f_1$, $f_2$, $f_3$, $f_4$, ...), i.e., ($P_{f1}$, $M_{f1}$, $P_{f2}$, $M_{f2}$, $P_{f3}$, $M_{f3}$, $P_{f4}$, $M_{f4}$, ...) are acquired. These measurements are used to obtain values for the variables (Dwall, Lblood, mua, musp) that are in turn used to specify the appropriate calibration curve. The calibration curve is then used to obtain an arterial blood oxygen saturation ($S_aO_2$) value from the pulsatile measurements.

Figure 13:
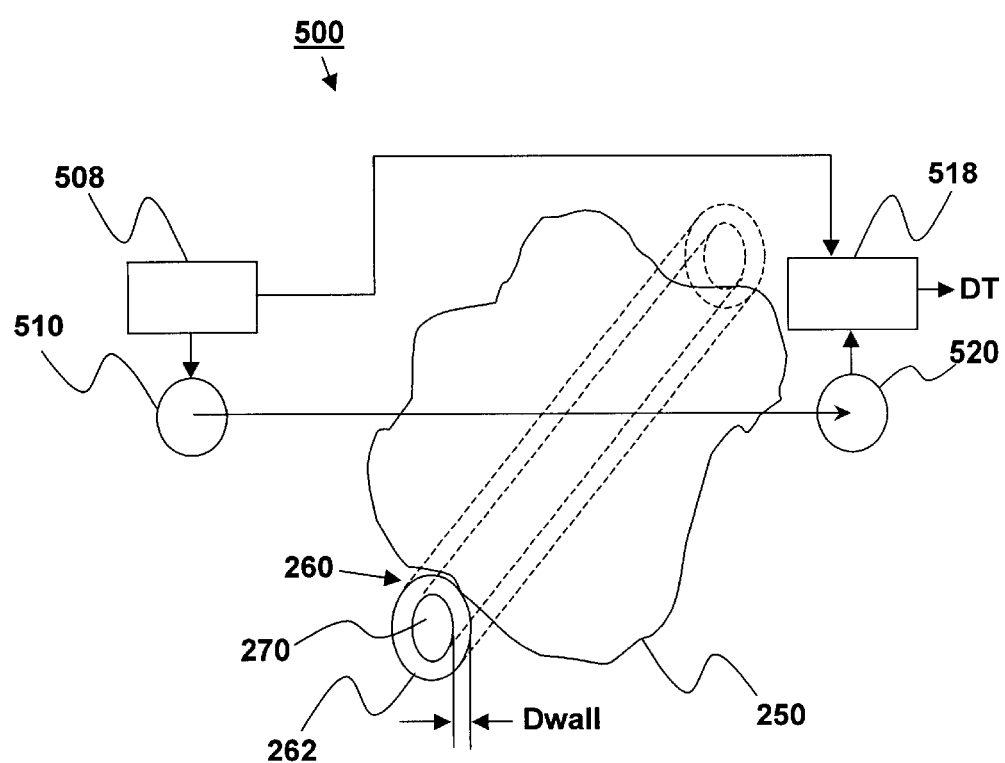
FIG. 13 is a schematic diagram illustrating use of an oximetry device configured to correlate a detected light transmission with a digitally modulated light stream to obtain measurements for calculating a blood oxygen saturation level according to a still further extended embodiment of the present invention.

In a still further improvement of the invention, illustrated schematically in FIG. 13, the light source 510 is modulated digitally as a unique stream of pulses of variable pulse duration using a digital modulator 508. Or the stream of pulses from the modulator 508 may be a pseudorandom sequence of uniform-duration pulses. The detector 520 acquires the signal and uses a correlator 518 (e.g., a specially programmed microprocessor) to decode the received pulse stream and correlate it against the known source stream to specify the delay time DT for transmission to the detector. The pulse durations are preferably very short, such as between 1ns to 1 $\mu$s.

The delay times associated with transmission between a set of source and detectors yields a set of measurements (DT1, DT2, DT3, DT4, DT5, ...) that in turn specify values for the variables (Dwall, Lblood, mua, musp). These variables are used to specify the appropriate calibration curve to allow the pulsatile measurements to yield an arterial blood oxygen saturation ($S_aO_2$) value. The foregoing two improvements could also involve a combination of variable wavelengths and/or source-detector separations and positions, as described above.

Oximetry devices other than surgically-implanted devices to monitor oxygenation in a blood vessel could also be used. For example, an oximetry device could be implanted to monitor the oxygenation of a specific organ. Depending on the application, the geometry and complexity of the situation may involve a set of variables, here called (x1, x2, x3, x4, ...), that are similar to, but different from the previously identified variables (Dwall, Lblood, mua, musp).

In this case, as with the other improved embodiments described previously, a plurality of wavelengths and source-detector separations and positions, or different frequencies of modulations or variable digital streams controlling light sources can be used to determine the nonpulsatile component of a set of light transmission measurements (m1, m2, m3, m4, m5, ...). These measurements can then be used to determine values for the parameters (x1, x2, x3, x4, ...) that are in turn used select an appropriate calibration curve. The calibration curve then allows interpretation of the pulsatile component of transmission measurements to yield an arterial blood oxygen saturation ($S_aO_2$) value.

Having described and illustrated the principles of and improvements to the invention in various embodiments thereof, it should be apparent that the invention can be modified in arrangement and detail without departing from such principles. I therefore claim all modifications and variations coming within the spirit and scope of the following claims.

What is claimed is:

1. A method of calibrating an oximeter and determining an arterial blood oxygen saturation level in tissue, comprising:

using a plurality of measurements to determine properties of a light transmission passing through or reflected from a tissue; and using the properties of the light transmission or reflection to select a calibration curve, said calibration curve representing a level of arterial blood oxygen saturation in relation to a pulsatile factor;

wherein the plurality of measurements is obtained by varying a position of a light source or a light detector relative to the tissue to detect light passed through or reflected from different portions of the tissue.

2. A method according to claim 1, wherein the plurality of measurements is obtained by using two or more light sources and at least one light detector.

3. A method according to claim 1, wherein the plurality of measurements is obtained by using at least one light source and two or more detectors.

4. A method of calibrating an oximeter and determining an arterial blood oxygen saturation level in tissue, comprising:

using a plurality of measurements to determine properties of a light transmission passing through or reflected from a tissue; and using the properties of the light transmission or reflection to select a calibration curve, said calibration curve representing a level of arterial blood oxygen saturation in relation to a pulsatile factor;

wherein the plurality of measurements is obtained by modulating a light source being supplied to the tissue.

5. A method according to claim 4, wherein the light source is modulated at various frequencies between 50 kHz and 1 GHz, and wherein the phase and modulation of the transmitted light are measured.

6. A method according to claim 5, further comprising using the phase and modulation measurements to determine the properties of the light transmission used to select the calibration curve.

7. A method according to claim 4, wherein the plurality of measurements is obtained by digitally modulating a light source transmitted through or reflected from the tissue.

8. A method according to claim 7 wherein the light source is digitally modulated as a unique source stream of pulses of variable pulse duration.

9. A method according to claim 7, wherein the light source is digitally modulated with pulse durations of an order of magnitude approximately between 1 ns and 1 $\mu$s.

10. A method according to claim 7, further comprising detecting the light transmitted from the light source through or reflected from the tissue and correlating the detected light to the source stream of pulses to determine a delay time.

11. A method of calibrating an oximeter and determining an arterial blood oxygen saturation level in tissue, comprising:

using a plurality of measurements to determine properties of a light transmission passing through or reflected from a tissue; and using the properties of the light transmission or reflection to select a calibration curve, said calibration curve representing a level of arterial blood oxygen saturation in relation to a pulsatile factor;

wherein the properties of the light transmission comprise values for a plurality of variables, said variables comprising a vessel wall thickness, an average path length of photons, and optical properties of the tissue.

12. A method of calibrating an oximeter and determining an arterial blood oxygen saturation level in tissue, comprising:

using a plurality of measurements to determine properties of a light transmission passing through or reflected from a tissue;

using the properties of the light transmission or reflection to select a calibration curve, said calibration curve representing a level of arterial blood oxygen saturation in relation to a pulsatile factor; and normalizing a steady-state component of the light transmission or reflection to remove the effects of variation of a strength of a light source and a sensitivity of a transducer from the steady-state component.

* * * * *

UNITED STATES PATENT AND TRADEMARK OFFICE
CERTIFICATE OF CORRECTION

PATENT NO.     : 6,760,609 B2
DATED          : July 9, 2004
INVENTOR(S)    : Jacques It is certified that error appears in the above-identified patent and that said Letters Patent is hereby corrected as shown below:

Column 7,
Line 46, "at two, wavelengths" should read -- at two wavelengths --.

Column 12,
Line 22, "http//omlc.ogi." should read -- http://omlc.ogi. --.

Column 17,
Line 5, "(940 mm)" should read -- (940 nm) --.
Line 59, "R value. from" should read -- R value from --.

Column 18,
Line 59, "($\mu_a, \mu_s$')" should read -- ($\mu_a, \mu_s$'). --.

Column 26,
Line 30, "between Ins to 1 $\mu$s." should read -- between 1 ns to 1 $\mu$s. --.

Signed and Sealed this

Twenty-eighth Day of December, 2004

JON W. DUDAS
*Director of the United States Patent and Trademark Office*